United States Patent
Hansell et al.

(10) Patent No.: US 10,314,717 B2
(45) Date of Patent: Jun. 11, 2019

(54) EXPANDABLE VERTEBRAL PROSTHESIS

(71) Applicant: GLOBUS MEDICAL, INC., Audubon, PA (US)

(72) Inventors: Noah Hansell, King of Prussia, PA (US); Marcin Niemiec, Bridgeport, PA (US); William S. Rhoda, Media, PA (US)

(73) Assignee: Globus Medical, Inc., Audubon, PA (US)

( * ) Notice: Subject to any disclaimer, the term of this patent is extended or adjusted under 35 U.S.C. 154(b) by 137 days.

(21) Appl. No.: 14/873,576

(22) Filed: Oct. 2, 2015

(65) Prior Publication Data

US 2016/0022435 A1  Jan. 28, 2016

Related U.S. Application Data

(63) Continuation of application No. 14/157,017, filed on Jan. 16, 2014, now Pat. No. 9,173,747, which is a
(Continued)

(51) Int. Cl.
*A61F 2/44* (2006.01)
*A61F 2/46* (2006.01)
(Continued)

(52) U.S. Cl.
CPC .............. *A61F 2/4425* (2013.01); *A61F 2/44* (2013.01); *A61F 2/442* (2013.01); *A61F 2/4611* (2013.01); *A61F 2002/2817* (2013.01); *A61F 2002/2835* (2013.01); *A61F 2002/3041* (2013.01); *A61F 2002/3052* (2013.01); *A61F 2002/3055* (2013.01); *A61F 2002/30235* (2013.01); *A61F 2002/30369* (2013.01); *A61F 2002/30405* (2013.01); *A61F 2002/30495* (2013.01); *A61F 2002/30507* (2013.01); *A61F 2002/30525* (2013.01); *A61F 2002/30601* (2013.01);
(Continued)

(58) Field of Classification Search
CPC ....... A61F 2/446; A61F 2/4455; A61F 2/4611
See application file for complete search history.

(56) References Cited

U.S. PATENT DOCUMENTS

| 518,213 A | 4/1894 | Ball |
| 2,580,482 A | 1/1952 | Stukenborg et al. |

(Continued)

FOREIGN PATENT DOCUMENTS

WO   WO 2010027359 A1 *   3/2010   ............... A61F 2/44

*Primary Examiner* — Ellen C Hammond

(57) ABSTRACT

The present invention relates to an expandable prosthetic implant device for engagement between vertebrae generally comprising an inner member, outer member, gear member and a locking assembly positioned coaxial with respect to each other such that the inner and outer members are moveable relative to each other along an axis. The gear member is axially fixed to the outer member and freely rotatable with respect to the outer member and the gear member threadedly engages a threaded portion of the inner member to translate inner member along the axis. The implant is configured to engage the vertebrae in a predetermined alignment and the gear member includes gear teeth exposed to the exterior and configured to be accessible by a tool member at a plurality of angular positions around the perimeter of the implant device.

18 Claims, 31 Drawing Sheets

Related U.S. Application Data continuation of application No. 12/352,163, filed on Jan. 12, 2009, now Pat. No. 8,721,723.

(51) Int. Cl.
  A61F 2/28 (2006.01)
  A61F 2/30 (2006.01)

(52) U.S. Cl.
  CPC ........... *A61F 2002/30616* (2013.01); *A61F 2002/30624* (2013.01); *A61F 2002/30649* (2013.01); *A61F 2002/30777* (2013.01); *A61F 2002/30841* (2013.01); *A61F 2002/4475* (2013.01); *A61F 2002/4627* (2013.01); *A61F 2002/4628* (2013.01); *A61F 2002/4629* (2013.01); *A61F 2220/0025* (2013.01); *A61F 2220/0033* (2013.01); *A61F 2230/0069* (2013.01)

(56) References Cited

U.S. PATENT DOCUMENTS

| | | |
|---|---|---|
| 2,694,586 A | 11/1954 | Smith |
| 2,794,474 A | 6/1957 | Stukenborg |
| 2,843,408 A | 7/1958 | Stukenborg |
| 3,486,505 A | 12/1969 | Gordon |
| 3,719,186 A | 3/1973 | Merig, Jr. |
| 3,741,205 A | 6/1973 | Markolf |
| 3,848,601 A | 11/1974 | Ma |
| 3,905,047 A | 9/1975 | Long |
| 3,916,907 A | 11/1975 | Peterson |
| 4,156,296 A | 5/1979 | Johnson |
| 4,177,524 A | 12/1979 | Grell |
| 4,289,123 A | 9/1981 | Dunn |
| 4,309,777 A | 1/1982 | Patil |
| 4,401,112 A * | 8/1983 | Rezaian ............. A61F 2/44 606/279 |
| 4,484,570 A | 11/1984 | Sutter |
| 4,501,269 A | 2/1985 | Bagby |
| 4,512,038 A | 4/1985 | Alexander |
| 4,537,185 A | 8/1985 | Stednitz |
| 4,545,374 A | 10/1985 | Jacobson |
| 4,553,273 A | 11/1985 | Wu |
| 4,554,914 A | 11/1985 | Kapp |
| 4,573,448 A | 3/1986 | Kambin |
| 4,599,086 A | 7/1986 | Doty |
| 4,611,581 A | 9/1986 | Steffee |
| 4,611,582 A | 9/1986 | Duff |
| 4,636,217 A | 1/1987 | Ogilvie |
| 4,645,503 A | 2/1987 | Lin |
| 4,657,550 A * | 4/1987 | Daher ............. A61F 2/44 606/246 |
| 4,677,972 A | 7/1987 | Tornier |
| 4,696,290 A | 9/1987 | Steffee |
| 4,743,256 A | 5/1988 | Brantigan |
| 4,759,766 A | 7/1988 | Buettner-Janz |
| 4,772,287 A | 9/1988 | Ray |
| 4,820,305 A | 4/1989 | Harms et al. |
| 4,834,757 A | 5/1989 | Brantigan |
| 4,863,476 A | 9/1989 | Shepperd |
| 4,863,477 A | 9/1989 | Monson |
| 4,874,389 A | 10/1989 | Downey |
| 4,877,020 A | 10/1989 | Vich |
| 4,878,915 A | 11/1989 | Brantigan |
| 4,880,343 A | 11/1989 | Matsumoto |
| 4,892,546 A | 1/1990 | Kotz |
| 4,903,690 A | 2/1990 | Campbell |
| 4,911,718 A | 3/1990 | Lee et al. |
| 4,927,421 A | 5/1990 | Goble et al. |
| 4,932,975 A | 6/1990 | Main et al. |
| 4,936,848 A | 6/1990 | Bagby |
| 4,945,127 A | 7/1990 | Kagawa et al. |
| 4,950,258 A | 8/1990 | Kawai et al. |
| 4,950,269 A | 8/1990 | Gaines, Jr. |
| 4,950,270 A | 8/1990 | Bowman et al. |
| 4,961,740 A | 10/1990 | Ray et al. |
| 5,012,247 A | 4/1991 | Dillman |
| 5,015,247 A | 5/1991 | Michelson |
| 5,015,255 A | 5/1991 | Kulich |
| 5,019,108 A | 5/1991 | Bertin et al. |
| 5,026,373 A | 6/1991 | Ray et al. |
| 5,042,588 A | 8/1991 | Herchenbach et al. |
| 5,055,104 A | 10/1991 | Ray |
| 5,057,109 A | 10/1991 | Olerud |
| 5,059,193 A | 10/1991 | Kuslich |
| 5,062,845 A | 11/1991 | Kuslich et al. |
| 5,062,850 A | 11/1991 | MacMillan et al. |
| 5,064,425 A | 11/1991 | Branemark et al. |
| 5,071,437 A | 12/1991 | Steffee |
| 5,108,395 A | 4/1992 | Laurain |
| 5,123,926 A | 6/1992 | Pisharodi |
| 5,139,499 A | 8/1992 | Small et al. |
| 5,147,402 A | 9/1992 | Bohler et al. |
| 5,147,404 A | 9/1992 | Downey |
| 5,171,278 A | 12/1992 | Pisharodi |
| 5,171,280 A | 12/1992 | Baumgartner |
| 5,189,110 A | 2/1993 | Ikematu |
| 5,192,237 A | 3/1993 | Pegoraro |
| 5,192,326 A | 3/1993 | Bao et al. |
| 5,192,327 A | 3/1993 | Brantigan |
| 5,195,541 A | 3/1993 | Obenchain |
| 5,236,460 A * | 8/1993 | Barber ............. A61F 2/44 403/109.7 |
| 5,258,031 A | 11/1993 | Salib et al. |
| 5,263,953 A | 11/1993 | Bagby |
| 5,290,289 A | 3/1994 | Sanders et al. |
| 5,290,312 A | 3/1994 | Kojimoto et al. |
| 5,300,076 A | 4/1994 | Leriche |
| 5,306,310 A | 4/1994 | Siebels |
| 5,313,962 A | 5/1994 | Obenchain |
| 5,330,535 A | 7/1994 | Moser et al. |
| 5,336,223 A | 8/1994 | Rogers |
| 5,354,302 A | 10/1994 | Ko |
| 5,357,983 A | 10/1994 | Matthews |
| 5,358,524 A | 10/1994 | Richelsoph |
| 5,360,430 A | 11/1994 | Lin |
| 5,364,397 A | 11/1994 | Hayes et al. |
| 5,382,226 A | 1/1995 | Graham |
| 5,390,683 A | 2/1995 | Pisharodi |
| 5,395,317 A | 3/1995 | Kambin |
| 5,413,602 A | 5/1995 | Metz-Stavenhagen |
| 5,423,816 A | 6/1995 | Lin |
| 5,423,817 A | 6/1995 | Lin |
| 5,425,772 A | 6/1995 | Brantigan |
| 5,429,447 A | 7/1995 | Wood |
| 5,431,658 A | 7/1995 | Moskovich |
| 5,439,464 A | 8/1995 | Shapiro |
| 5,443,514 A | 8/1995 | Steffee |
| 5,443,515 A | 8/1995 | Cohen et al. |
| 5,445,639 A | 8/1995 | Kuslich et al. |
| 5,458,638 A | 10/1995 | Kuslich et al. |
| 5,458,641 A * | 10/1995 | Ramirez Jimenez ..... A61F 2/44 403/43 |
| 5,458,642 A | 10/1995 | Beer et al. |
| 5,480,442 A | 1/1996 | Bertagnoli |
| 5,482,417 A | 1/1996 | Erickson |
| 5,484,437 A | 1/1996 | Michelson |
| 5,489,307 A | 2/1996 | Kuslich et al. |
| 5,489,308 A | 2/1996 | Kuslich et al. |
| 5,505,732 A | 4/1996 | Michelson |
| 5,522,899 A | 6/1996 | Michelson |
| 5,533,863 A | 7/1996 | Tornquist et al. |
| 5,534,028 A | 7/1996 | Bao et al. |
| 5,534,029 A | 7/1996 | Shima |
| 5,534,031 A | 7/1996 | Matsuzaki et al. |
| 5,540,689 A | 7/1996 | Sanders et al. |
| 5,549,608 A | 8/1996 | Errico et al. |
| 5,549,679 A | 8/1996 | Kuslich |
| 5,554,191 A | 9/1996 | Lahille et al. |
| 5,562,736 A | 10/1996 | Ray et al. |
| 5,569,176 A | 10/1996 | Graham |
| 5,571,109 A | 11/1996 | Bertagnoli |
| 5,571,189 A | 11/1996 | Kuslich |

(56) References Cited

U.S. PATENT DOCUMENTS

| | | | |
|---|---|---|---|
| 5,571,192 A * | 11/1996 | Schonhoffer | A61F 2/44 606/247 |
| 5,575,790 A | 11/1996 | Chen et al. | |
| 5,591,235 A | 1/1997 | Kuslich | |
| 5,603,713 A | 2/1997 | Aust et al. | |
| 5,603,722 A | 2/1997 | Phan et al. | |
| 5,607,474 A | 3/1997 | Athanasiou et al. | |
| 5,653,763 A | 8/1997 | Errico et al. | |
| 5,658,335 A | 8/1997 | Allen | |
| 5,658,336 A | 8/1997 | Pisharodi | |
| 5,665,122 A | 9/1997 | Kambin | |
| 5,674,286 A | 10/1997 | D'Alessio et al. | |
| 5,674,295 A | 10/1997 | Ray et al. | |
| 5,676,699 A | 10/1997 | Gogolewski et al. | |
| 5,683,465 A | 11/1997 | Shinn et al. | |
| 5,693,100 A | 12/1997 | Pisharodi | |
| 5,702,449 A | 12/1997 | McKay | |
| 5,702,453 A * | 12/1997 | Rabbe | A61B 17/70 606/247 |
| 5,702,455 A * | 12/1997 | Saggar | A61F 2/44 623/17.15 |
| 5,713,841 A | 2/1998 | Graham | |
| 5,716,410 A | 2/1998 | Wang et al. | |
| 5,716,416 A | 2/1998 | Lin | |
| 5,720,746 A | 2/1998 | Soubeiran | |
| 5,723,013 A * | 3/1998 | Jeanson | A61F 2/44 606/249 |
| 5,749,916 A | 5/1998 | Richelsoph | |
| 5,765,957 A | 6/1998 | Connell | |
| 5,776,197 A | 7/1998 | Rabbe et al. | |
| 5,776,198 A * | 7/1998 | Rabbe | A61B 17/70 606/247 |
| 5,782,432 A | 7/1998 | Renshaw | |
| 5,800,433 A | 9/1998 | Benzel | |
| 5,823,699 A | 10/1998 | Austin, Jr. et al. | |
| 5,824,093 A | 10/1998 | Ray et al. | |
| 5,836,948 A | 11/1998 | Zucherman et al. | |
| 5,843,082 A | 12/1998 | Yuan et al. | |
| 5,860,977 A | 1/1999 | Zucherman et al. | |
| 5,861,035 A | 1/1999 | Griffith | |
| 5,863,297 A | 1/1999 | Walter et al. | |
| 5,868,745 A | 2/1999 | Alleyne | |
| 5,868,746 A | 2/1999 | Sarver | |
| 5,876,404 A | 3/1999 | Zucherman et al. | |
| 5,888,220 A | 3/1999 | Felt et al. | |
| 5,888,224 A | 3/1999 | Beckers et al. | |
| 5,895,428 A | 4/1999 | Berry | |
| 5,899,904 A | 5/1999 | Errico et al. | |
| 5,899,905 A | 5/1999 | Errico et al. | |
| 5,919,234 A | 7/1999 | Lemperle et al. | |
| 5,954,744 A | 9/1999 | Phan et al. | |
| 5,964,760 A | 10/1999 | Richelsoph | |
| 5,976,186 A | 11/1999 | Bao et al. | |
| 5,976,187 A | 11/1999 | Richelsoph | |
| 5,980,522 A | 11/1999 | Koros et al. | |
| 5,980,572 A | 11/1999 | Kim et al. | |
| 5,984,967 A | 11/1999 | Zdeblick et al. | |
| 5,989,290 A * | 11/1999 | Biedermann | A61F 2/44 606/246 |
| 5,989,291 A | 11/1999 | Ralph et al. | |
| 6,015,436 A * | 1/2000 | Schonhoffer | A61F 2/44 623/17.11 |
| 6,017,345 A | 1/2000 | Richelsoph | |
| 6,017,366 A | 1/2000 | Berman | |
| 6,019,793 A | 2/2000 | Perren et al. | |
| 6,022,352 A | 2/2000 | Vandewalle | |
| 6,024,764 A | 2/2000 | Schroeppel | |
| 6,036,693 A | 3/2000 | Yuan et al. | |
| 6,039,761 A | 3/2000 | Li et al. | |
| 6,045,579 A | 4/2000 | Hochschuler | |
| 6,048,342 A | 4/2000 | Zucherman et al. | |
| 6,068,630 A | 5/2000 | Zucherman et al. | |
| 6,071,982 A | 6/2000 | Wise et al. | |
| 6,074,390 A | 6/2000 | Zucherman et al. | |
| 6,086,613 A | 7/2000 | Camino et al. | |
| 6,090,112 A | 7/2000 | Zucherman et al. | |
| 6,090,996 A | 7/2000 | Li | |
| 6,093,205 A | 7/2000 | McLeod et al. | |
| 6,102,932 A | 8/2000 | Kurz | |
| 6,102,933 A | 8/2000 | Lee et al. | |
| 6,126,689 A | 10/2000 | Brett | |
| 6,127,597 A | 10/2000 | Beyar | |
| 6,132,432 A | 10/2000 | Richelsoph | |
| 6,132,465 A | 10/2000 | Ray et al. | |
| 6,136,031 A | 10/2000 | Middleton | |
| 6,149,652 A | 11/2000 | Zucherman et al. | |
| 6,152,926 A | 11/2000 | Zucherman et al. | |
| 6,156,038 A | 12/2000 | Zucherman et al. | |
| 6,156,842 A | 12/2000 | Hoenig et al. | |
| 6,159,244 A | 12/2000 | Suddaby | |
| 6,160,084 A | 12/2000 | Langer et al. | |
| 6,174,334 B1 | 1/2001 | Suddaby | |
| 6,176,881 B1 * | 1/2001 | Schar | A61F 2/44 606/309 |
| 6,177,883 B1 | 1/2001 | Jennetti et al. | |
| 6,179,873 B1 | 1/2001 | Zientek | |
| 6,183,471 B1 | 2/2001 | Zucherman et al. | |
| 6,187,048 B1 | 2/2001 | Milner et al. | |
| 6,190,387 B1 | 2/2001 | Zucherman et al. | |
| 6,190,413 B1 | 2/2001 | Sutcliffe | |
| 6,190,414 B1 | 2/2001 | Young et al. | |
| 6,193,720 B1 | 2/2001 | Yuan et al. | |
| 6,193,756 B1 | 2/2001 | Studer et al. | |
| 6,193,757 B1 | 2/2001 | Foley et al. | |
| 6,200,322 B1 | 3/2001 | Branch et al. | |
| 6,200,348 B1 | 3/2001 | Biedermann et al. | |
| 6,206,883 B1 | 3/2001 | Tunc | |
| 6,206,923 B1 | 3/2001 | Boyd et al. | |
| 6,214,005 B1 | 4/2001 | Benzel et al. | |
| 6,217,579 B1 | 4/2001 | Koros | |
| 6,221,075 B1 | 4/2001 | Tormala et al. | |
| 6,235,030 B1 | 5/2001 | Zucherman et al. | |
| 6,238,397 B1 | 5/2001 | Zucherman et al. | |
| 6,248,131 B1 | 6/2001 | Felt et al. | |
| 6,261,289 B1 | 7/2001 | Levy | |
| 6,264,695 B1 | 7/2001 | Stoy | |
| 6,280,444 B1 | 8/2001 | Zucherman et al. | |
| 6,332,882 B1 | 12/2001 | Zucherman et al. | |
| 6,332,883 B1 | 12/2001 | Zucherman et al. | |
| 6,332,895 B1 | 12/2001 | Suddaby | |
| 6,344,057 B1 | 2/2002 | Rabbe et al. | |
| 6,358,254 B1 | 3/2002 | Anderson | |
| 6,368,351 B1 | 4/2002 | Glenn et al. | |
| 6,375,682 B1 | 4/2002 | Fleischmann et al. | |
| 6,379,355 B1 | 4/2002 | Zucherman et al. | |
| 6,395,031 B1 | 5/2002 | Foley et al. | |
| 6,402,750 B1 | 6/2002 | Atkinson et al. | |
| 6,409,766 B1 | 6/2002 | Brett | |
| 6,419,676 B1 | 7/2002 | Zucherman et al. | |
| 6,419,677 B2 | 7/2002 | Zucherman et al. | |
| 6,425,919 B1 | 7/2002 | Lambrecht | |
| 6,428,544 B1 | 8/2002 | Ralph et al. | |
| 6,436,102 B1 | 8/2002 | Ralph et al. | |
| 6,436,140 B1 | 8/2002 | Liu et al. | |
| 6,436,143 B1 | 8/2002 | Ross et al. | |
| 6,443,989 B1 | 9/2002 | Jackson | |
| 6,451,019 B1 | 9/2002 | Zucherman et al. | |
| 6,451,020 B1 | 9/2002 | Zucherman et al. | |
| 6,451,057 B1 | 9/2002 | Chen et al. | |
| 6,454,769 B2 | 9/2002 | Wagner et al. | |
| 6,454,806 B1 | 9/2002 | Cohen et al. | |
| 6,454,807 B1 | 9/2002 | Jackson | |
| 6,468,310 B1 | 10/2002 | Ralph et al. | |
| 6,471,725 B1 | 10/2002 | Ralph et al. | |
| 6,478,796 B2 | 11/2002 | Zucherman et al. | |
| 6,482,234 B1 | 11/2002 | Weber et al. | |
| 6,482,235 B1 | 11/2002 | Lambrecht et al. | |
| 6,485,517 B1 | 11/2002 | Michelson | |
| 6,488,682 B2 | 12/2002 | Kikuchi et al. | |
| 6,488,683 B2 | 12/2002 | Lieberman | |
| 6,488,710 B2 | 12/2002 | Besselink | |
| 6,491,724 B1 | 12/2002 | Ferree | |
| 6,500,178 B2 | 12/2002 | Zucherman et al. | |

(56) References Cited

U.S. PATENT DOCUMENTS

| | | |
|---|---|---|
| 6,500,205 B1 | 12/2002 | Michelson |
| 6,508,839 B1 | 1/2003 | Lambrecht et al. |
| 6,514,256 B2 | 2/2003 | Zucherman et al. |
| 6,520,991 B2 | 2/2003 | Huene |
| 6,524,341 B2 | 2/2003 | Lang et al. |
| 6,527,806 B2 | 3/2003 | Ralph et al. |
| 6,551,319 B2 | 4/2003 | Lieberman |
| 6,551,320 B2 | 4/2003 | Lieberman |
| 6,558,390 B2 | 5/2003 | Cragg |
| 6,562,074 B2 | 5/2003 | Gerbec et al. |
| 6,569,203 B1 | 5/2003 | Keller |
| 6,582,467 B1 | 6/2003 | Teitelbaum et al. |
| 6,607,559 B2 | 8/2003 | Ralph et al. |
| 6,613,089 B1 | 9/2003 | Estes et al. |
| 6,648,917 B2 | 11/2003 | Gerbec et al. |
| 6,652,584 B2 | 11/2003 | Michelson |
| 6,660,038 B2 | 12/2003 | Boyer, II et al. |
| 6,666,891 B2 | 12/2003 | Boehm, Jr. et al. |
| 6,699,246 B2 | 3/2004 | Zucherman et al. |
| 6,699,247 B2 | 3/2004 | Zucherman et al. |
| 6,709,458 B2 | 3/2004 | Michelson |
| 6,712,852 B1 | 3/2004 | Chung et al. |
| 6,716,216 B1 | 4/2004 | Boucher et al. |
| 6,716,247 B2 | 4/2004 | Michelson |
| 6,719,796 B2 | 4/2004 | Cohen et al. |
| 6,723,126 B1 | 4/2004 | Berry |
| 6,730,088 B2 * | 5/2004 | Yeh ............ A61F 2/44 606/247 |
| 6,730,126 B2 | 5/2004 | Boehm, Jr. et al. |
| 6,733,534 B2 | 5/2004 | Sherman |
| 6,740,119 B2 | 5/2004 | Ralph et al. |
| 6,743,255 B2 | 6/2004 | Ferree |
| 6,749,614 B2 | 6/2004 | Teitelbaum et al. |
| 6,752,832 B2 * | 6/2004 | Neumann ............ A61F 2/44 606/247 |
| 6,758,861 B2 | 7/2004 | Ralph et al. |
| 6,758,863 B2 | 7/2004 | Estes |
| 6,764,491 B2 | 7/2004 | Frey |
| 6,764,515 B2 | 7/2004 | Ralph |
| 6,773,460 B2 | 8/2004 | Jackson |
| 6,776,781 B1 | 8/2004 | Uwaydah |
| 6,866,682 B1 * | 3/2005 | An ............ A61F 2/44 623/17.11 |
| 6,902,579 B2 | 6/2005 | Harms |
| 6,953,477 B2 | 10/2005 | Berry |
| 6,972,019 B2 | 12/2005 | Michelson |
| 7,077,864 B2 | 7/2006 | Byrd |
| 7,135,043 B2 | 11/2006 | Nakahara |
| 7,384,431 B2 | 6/2008 | Berry |
| 7,442,209 B2 | 10/2008 | Michelson |
| 7,494,296 B2 | 2/2009 | Stable |
| 7,588,573 B2 | 9/2009 | Berry |
| 7,641,693 B2 | 1/2010 | Gutlin |
| 7,662,616 B2 | 2/2010 | Lechmann |
| 7,674,296 B2 | 3/2010 | Rhoda |
| 7,691,147 B2 | 4/2010 | Gutlin |
| 7,708,779 B2 | 5/2010 | Edie |
| 7,758,648 B2 | 7/2010 | Castleman |
| 7,776,091 B2 | 8/2010 | Mastrorio |
| 7,794,502 B2 | 9/2010 | Michelson |
| 7,811,327 B2 | 10/2010 | Hansell |
| 7,819,922 B2 | 10/2010 | Sweeney |
| 7,846,207 B2 | 12/2010 | Lechmann |
| 7,879,096 B2 | 2/2011 | Dickson |
| 7,909,870 B2 | 3/2011 | Kraus |
| 7,914,581 B2 | 3/2011 | Dickson |
| 7,972,363 B2 | 7/2011 | Moskowitz |
| 7,985,255 B2 | 7/2011 | Bray |
| 8,034,111 B2 | 10/2011 | Hsu |
| 2002/0161441 A1 * | 10/2002 | Lang ............ A61F 2/44 623/17.11 |
| 2003/0045877 A1 | 3/2003 | Yeh |
| 2003/0176925 A1 | 9/2003 | Paponneau |
| 2004/0073314 A1 | 4/2004 | White et al. |
| 2005/0004572 A1 | 1/2005 | Biedermann et al. |
| 2006/0004447 A1 * | 1/2006 | Mastrorio ............ A61B 17/7065 623/17.11 |
| 2006/0058877 A1 | 3/2006 | Gutlin |
| 2006/0100710 A1 * | 5/2006 | Gutlin ............ A61F 2/44 623/17.15 |
| 2006/0200244 A1 | 9/2006 | Assaker |
| 2006/0241762 A1 | 10/2006 | Kraus |
| 2006/0241770 A1 * | 10/2006 | Rhoda ............ A61F 2/44 623/17.15 |
| 2006/0293755 A1 | 12/2006 | Lindner |
| 2007/0191954 A1 | 8/2007 | Hansell |
| 2007/0250171 A1 | 10/2007 | Bonin |
| 2007/0255415 A1 | 11/2007 | Edie |
| 2008/0015698 A1 | 1/2008 | Marino et al. |
| 2008/0027553 A1 | 1/2008 | Zucherman et al. |
| 2008/0183293 A1 | 7/2008 | Parry |
| 2008/0243254 A1 | 10/2008 | Butler |
| 2008/0281424 A1 | 11/2008 | Parry |
| 2009/0112320 A1 | 4/2009 | Kraus |
| 2009/0112324 A1 | 4/2009 | Refai |
| 2009/0112325 A1 | 4/2009 | Refai |
| 2009/0138089 A1 | 5/2009 | Doubler |
| 2009/0164017 A1 | 6/2009 | Sommerich |
| 2009/0182430 A1 | 7/2009 | Tyber |
| 2009/0192613 A1 | 7/2009 | Wing |
| 2009/0210061 A1 | 8/2009 | Sledge |
| 2009/0234455 A1 | 9/2009 | Moskowitz |
| 2010/0094424 A1 | 4/2010 | Woodburn |
| 2010/0106251 A1 | 4/2010 | Kast |
| 2010/0145460 A1 | 6/2010 | McDonough |
| 2010/0179655 A1 | 7/2010 | Hansell |
| 2010/0249934 A1 | 9/2010 | Melkent |
| 2010/0274357 A1 | 10/2010 | Miller |
| 2010/0280614 A1 | 11/2010 | Castleman |
| 2010/0286787 A1 | 11/2010 | Villiers |
| 2010/0298942 A1 | 11/2010 | Hansell |
| 2010/0324686 A1 | 12/2010 | Gerner |
| 2010/0324687 A1 | 12/2010 | Melkent et al. |
| 2011/0015741 A1 | 1/2011 | Melkent et al. |
| 2011/0035009 A1 | 2/2011 | Sweeney |
| 2011/0087328 A1 | 4/2011 | Dickson |
| 2011/0178598 A1 * | 7/2011 | Rhoda ............ A61F 2/44 623/17.16 |
| 2011/0184524 A1 | 7/2011 | Wiedenbeck |
| 2011/0196493 A1 | 8/2011 | Pimenta |
| 2011/0218631 A1 * | 9/2011 | Woodburn, Sr. ............ A61F 2/442 623/17.16 |
| 2011/0251691 A1 | 10/2011 | McLaughlin |
| 2011/0251692 A1 | 10/2011 | McLaughlin |

\* cited by examiner

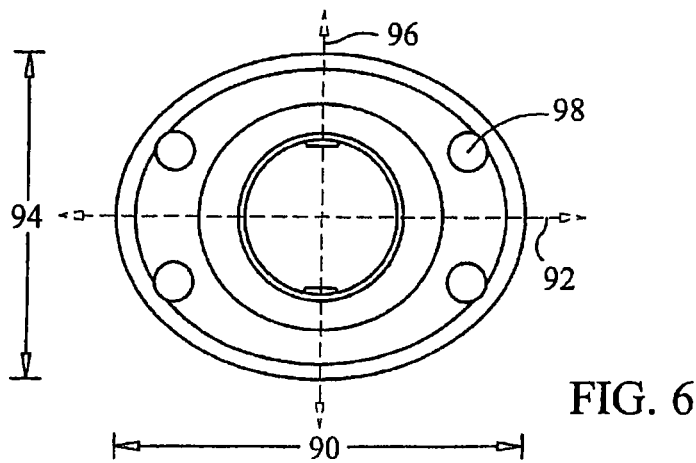
FIG. 6
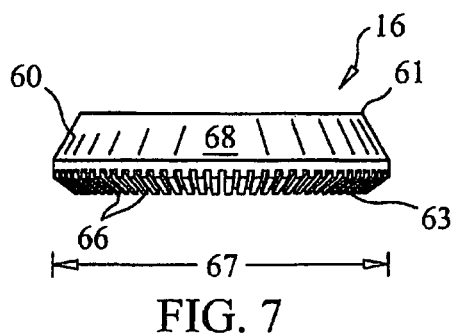
FIG. 7
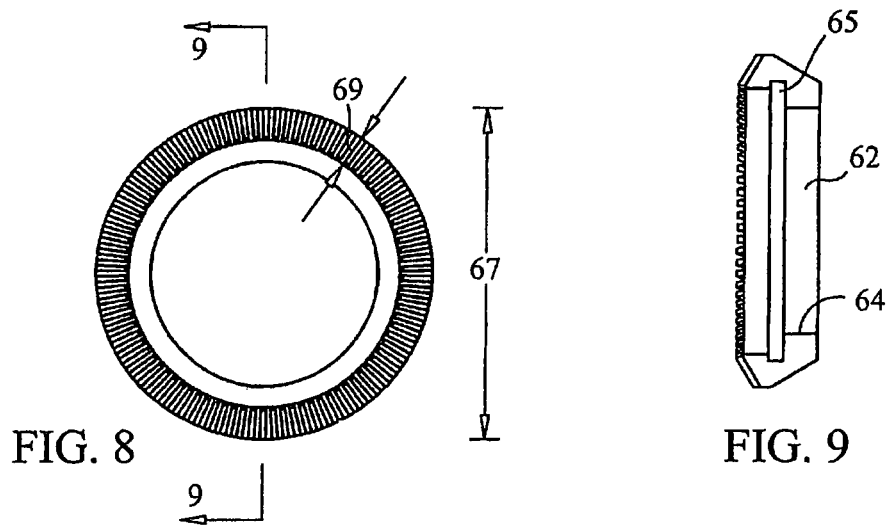
FIG. 8
FIG. 9

EXPANDABLE VERTEBRAL PROSTHESIS

CROSS REFERENCE TO RELATED APPLICATIONS

This application is a continuation of U.S. patent application Ser. No. 14/157,017, filed Jan. 16, 2014, which is a continuation of U.S. patent application Ser. No. 12/352,163, filed on Jan. 12, 2009, now U.S. Pat. No. 8,721,723, which are incorporated by reference herein in their entireties for all purposes.

FIELD OF THE INVENTION

The present invention relates to a device to support the spine after removal of at least a part of a vertebra.

BACKGROUND OF THE INVENTION

When a vertebra is damaged or diseased, surgery may be used to replace the vertebra or a portion thereof with a prosthetic device to restore spinal column support. For example, vertebral body replacement is commonly required in the treatment of vertebral fracture, tumor, or infection.

In recent years, several artificial materials and implants have been developed to replace the vertebral body, such as, for example, titanium cages, ceramic, ceramic/glass, plastic or PEEK, and carbon fiber spacers. Recently, various expandable prosthetics or expandable cages have been developed and used for vertebral body replacement. The expandable prosthetic devices are generally adjustable to the size of the cavity created by a corpectomy procedure and typically are at least partially hollow to accommodate bone cement or bone fragments to facilitate fusion in vivo. Some expandable prosthesis may be adjusted prior to insertion into the cavity, while others may be adjusted in situ. One advantage of the vertebral body replacement using an expandable prosthetic device that is adjustable in situ is that it is easy to place or insert because it permits an optimal, tight fit and correction of the deformity by in vivo expansion of the device. Some other advantages offered by an expandable prosthetic device are that they can facilitate distraction across the resected vertebral defect for correction of the deformity, and allow immediate load bearing after corpectomy.

Instrumentation and specialized tools for insertion of a vertebral implant is one important design parameter to consider when designing a vertebral prosthesis. Spinal surgery procedures can present several challenges because of the small clearances around the prosthetic when it is being inserted into position. Another important design consideration includes the ability of the device to accommodate various surgical approaches for insertion of the vertebral implant.

SUMMARY OF THE INVENTION

The present invention relates to an expandable prosthetic implant device for engagement between vertebrae generally comprising an inner member, outer member, and gear member positioned coaxial with respect to each other such that the inner and outer members are moveable relative to each other along an axis. The inner member has a hollow interior portion and a threaded external portion and includes a first end portion configured to engage a first vertebral body. The outer member has a hollow interior portion configured to receive the inner member and includes a second end portion configured to engage a second vertebral body. The gear member is axially fixed to the outer member and freely rotatable with respect to the outer member and the gear member threadedly engages the threaded portion of the inner member.

The implant is configured to engage the vertebrae such that first and second end portions are oriented in a predetermined alignment with respect to the first and second vertebral bodies. The gear member includes gear teeth extending around the perimeter of the gear member and the gear teeth are exposed to the exterior and configured to be accessible by a tool member at a plurality of angular positions around the perimeter.

In one embodiment, the outer member includes a plurality of tool location holes for receiving a portion of a tool member therein to facilitate insertion, alignment and engagement of the tool member with the gear teeth. In another variation, the outer member includes a resiliently deformable portion for receiving the gear member thereon. In yet another embodiment, the inner member, outer member, and gear member may be made of a PEEK plastic material. In another embodiment, the device also includes a locking member for fixing the inner member with respect to the outer member.

In one embodiment, the inner member is rotationally fixed with respect to the outer member. In one variation, the inner member includes a slot and a pin extends radially inward from the outer member to engage the slot to prevent rotational movement of the inner member with respect to the outer member.

In another embodiment, the first end portion may comprise a first plate having a generally oblong shape when viewed perpendicular to the longitudinal axis, the first plate extending a width distance along a long axis and a depth distance along a short axis, wherein the width distance is larger than the depth distance. Similarly, in another embodiment, the second end portion may comprise a second plate having a generally oblong shape when viewed perpendicular to the longitudinal axis, the second plate extending a width distance along a long axis and a depth distance along a short axis, wherein the width distance is larger than the depth distance. In one variation, the first and second end plates include at least one bone engaging member extending longitudinally from the end plates. The bone engaging members may comprise metal spikes.

In another variation, end portions have a thickness in the longitudinal direction and the thickness is variable in the anterior-posterior direction along the short axis. In one embodiment, the thickness varies gradually in the anterior-posterior direction such that the end portion defines a general wedge-shaped profile. In another embodiment, the end portion extends in the anterior-posterior direction from an anterior side to a posterior side and the first end portion has a first thickness at an anterior side and a second thickness at a posterior side, wherein the first thickness is greater than the second thickness. In yet another embodiment, the end portion includes a bone engaging surface and a plane tangent to the bone engaging surface intersects a plane normal to the longitudinal axis at a first angle. In one variation, the angle is between about −16 degrees and about 16 degrees.

BRIEF DESCRIPTION OF THE DRAWINGS

The invention will be more readily understood with reference to the embodiments thereof illustrated in the attached drawing figures, in which:

FIG. 6 is an end view of the prosthetic device of FIG. 1;

FIG. 7 is an elevated side view of one embodiment of a gear member of the prosthetic device of FIG. 1;

FIG. 8 is an end view of the gear member of FIG. 7;

FIG. 9 is a cross-sectional view of the gear member of FIGS. 7 and 8 taken along line 9-9 of FIG. 8;

Throughout the drawing figures, it should be understood that like numerals refer to like features and structures.

DETAILED DESCRIPTION OF THE INVENTION

Figure 1:
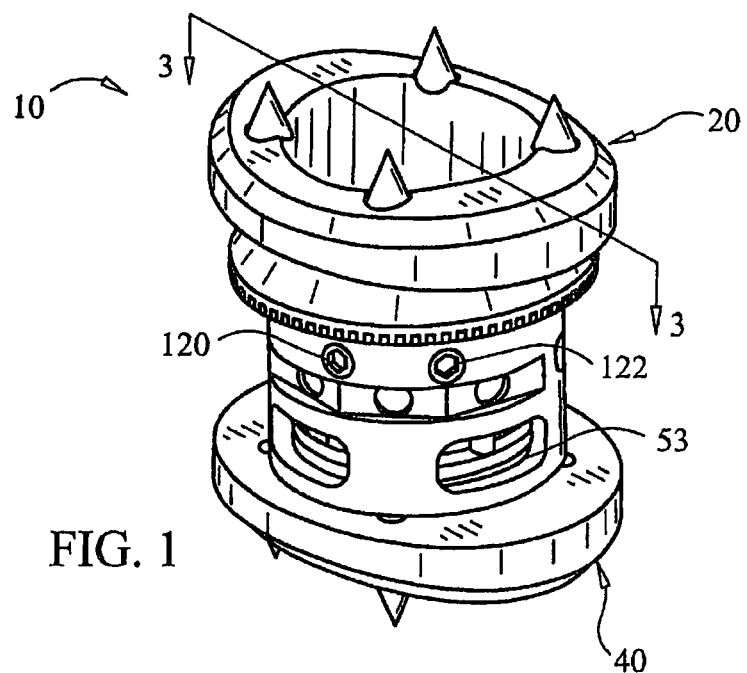
FIG. 1 is a perspective view of a prosthetic device in accordance with an embodiment of the invention.

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Referring to FIGS. 1-9, one embodiment of an expandable vertebral prosthetic device 10 is shown. Prosthesis 10 generally comprises an inner member 12 which may be telescopingly received within an outer member 14. The prosthesis 10 further comprises a gear member 16 generally configured to effect translation of inner member 12 with respect to outer member 14 and cause expansion of prosthesis 10. Inner member 12, outer member 14, and gear member 16 are centered along a longitudinal axis 18 and define a hollow interior portion which may be filled with bone material, bone growth factors, bone morphogenic proteins, or other materials for encouraging bone growth, blood vessel growth or growth of other tissue through the many apertures in the device. In one embodiment, members 12, 14, and 16 are made of a polyether ether ketone (PEEK) plastic material. Several known advantages of PEEK plastic material include that it is radiolucent and may be more easily sterilized than other plastics. In alternate embodiments, members 12, 14, and 16 may be made of a biologically inert metal alloy or other suitable materials.

Referring to FIGS. 1-4, inner member 12 has an endplate 20 at a distal end 22 connected to a generally cylindrical body 24 at a proximal end 26 and generally defines a hollow interior portion extending axially therethrough. Body 24 of inner member 12 generally comprises a wall 27 with an inner surface 28 and an outer surface 30 and at least part of outer surface 30 includes external threads 32. Outer diameter 34 of body 24 is dimensioned to be cooperatively received within outer member 14.

Outer member 14 has an endplate 40 at a proximal end 42 connected to a generally cylindrical body 44 at a distal end 46 and generally defines a hollow interior portion extending axially therethrough. Body 44 of outer member 14 generally comprises a wall 47 with an inner surface 48 and an outer surface 50. Inner diameter 52 of body 44 is dimensioned to cooperatively receive body 24 of inner member 12 within outer member 14. In this regard, inner diameter 52 of body 44 is greater than outer diameter 34 of body 24 of inner member 12. As shown in FIG. 1, outer member 14 may include one or more openings 53 to permit bone ingrowth. According to one embodiment, a lip 54 is formed around the exterior of the distal end 46 of body 44 and is configured to cooperatively fit with a portion of gear member 16. A plurality of relief spaces or slots 56 extending through wall 47 are angularly spaced around body 44 adjacent distal end 46 to facilitate a snapping engagement of lip 54 with gear member 16. In this regard, slots 56 allow distal end 46 to deform slightly and contract in the radial direction to accommodate gear member 16 to snap on to lip 54.

Figure 3:
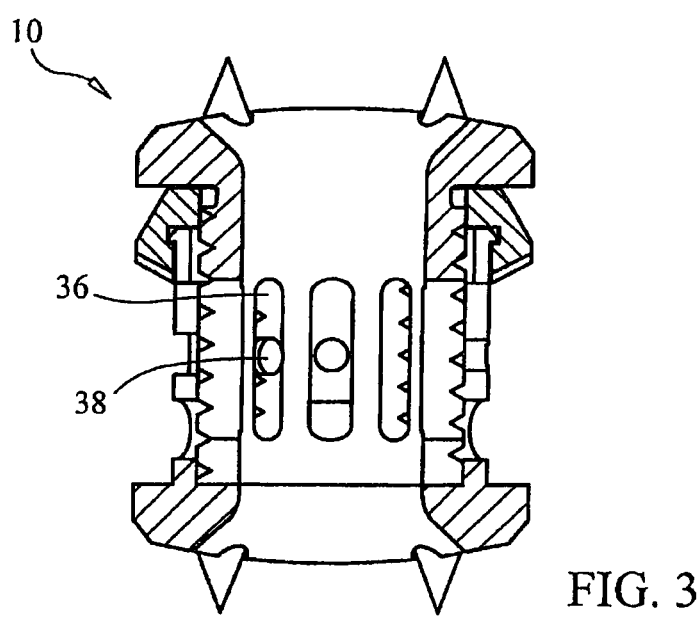
FIG. 3 is a cross-sectional view of the prosthetic device of FIG. 1 taken along line 3-3 of FIG. 1.
Figure 2:
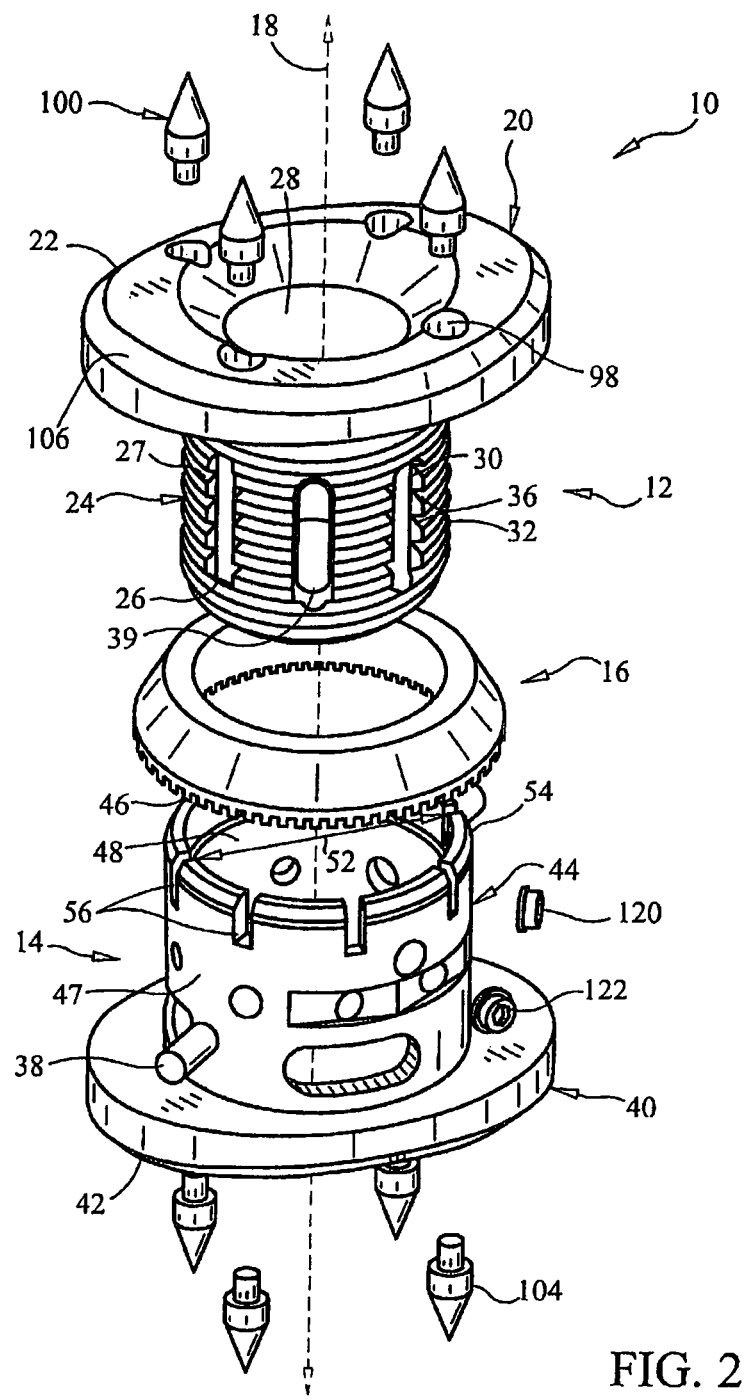
FIG. 2 is an exploded view of the prosthetic device of FIG. 1.
Figure 4:
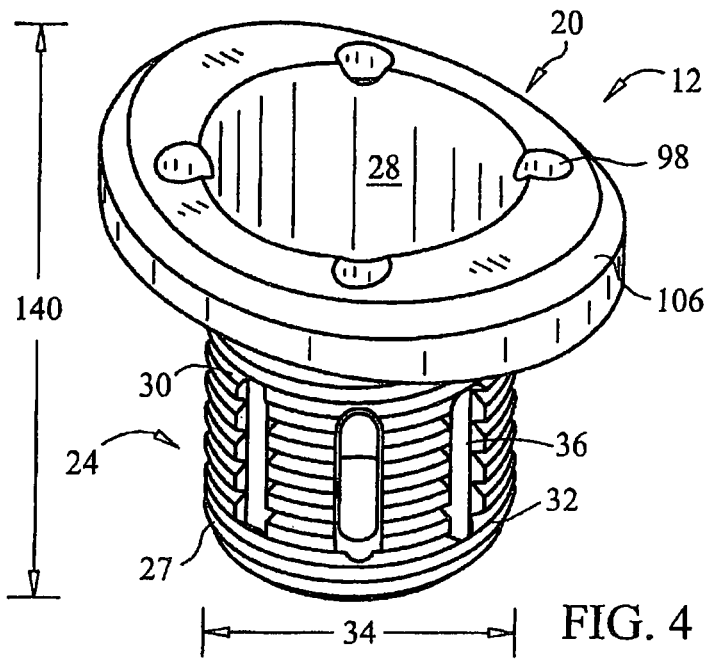
FIG. 4 is perspective view of an embodiment of an inner member of the prosthetic device of FIG. 1.
Figure 5:
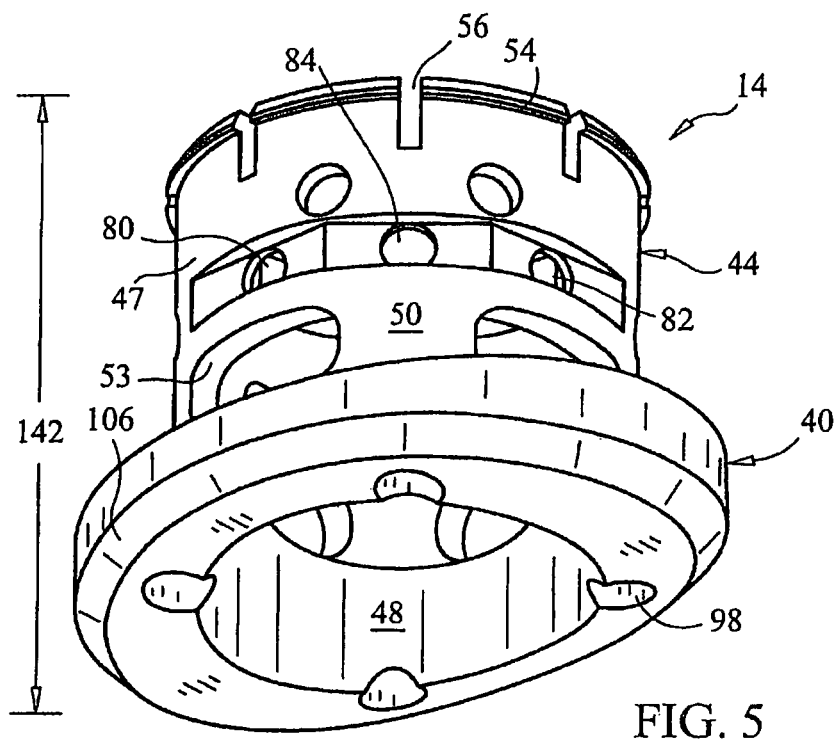
FIG. 5 is perspective view of an embodiment of an outer member of the prosthetic device of FIG. 1.

As best seen in FIGS. 2-4, in one embodiment of a prosthetic device 10, inner member 12 includes a plurality of longitudinal slots 36 extending radially through wall 27. Slots 36 are angularly spaced around body 24 and extend longitudinally along wall 27. When inner member 12 is assembled within outer member 14, slots 36 are configured to engage at least one pin 38 protruding radially inward from the inner surface 48 of outer member 14 to prevent rotational movement of inner member 12 with respect to outer member 14. In this regard, pin 38 may extend into one of slots 36 and may ride within one of the longitudinal slots 36 during expansion of the prosthetic device 10 to prevent rotation of inner member 12 with respect to outer member 14. In addition, pin 38 may prevent inner member 12 from expanding or translating along axis 18 beyond a predetermined distance when pin 38 bottoms out or contacts the proximal end 39 of the slot in which it is engaged.

Referring to FIGS. 7-9, gear member 16 comprises a generally hollow body 60 extending from a distal end 61 to a proximal end 63 with a helical thread 62 along at least part of an inner wall 64 and an array of gear teeth 66 along a portion of the exterior wall 68. Gear member 16 is generally configured to rotatably connect to distal end 46 of outer member 14 and internal helical thread 62 is configured to engage external threads 32 of inner member 12 to cause translation of inner member 12 with respect to outer member 14. In one embodiment, gear member 16 includes a cylindrical cutout feature 65 extending around the inner wall 64 to cooperatively receive lip 54 of outer member 14. In this regard, gear member 16 may rotate freely with respect to outer member 14 while being retained from longitudinal and lateral movement. In this regard, the aforementioned snap-on feature allows for the design and manufacture of a relatively thin walled outer member 14 to facilitate the creation of a larger inner diameter of outer gear member 16 and inner member 12. As a result, more bone growth stimulating material may be packed into the prosthetic device 10. Also, by creating a larger inner diameter of gear member 16 and inner member 12, a larger thread size for external thread 32 and internal thread 62 may be utilized to provide greater mechanical strength.

Referring to FIG. 7, gear teeth 66 are positioned at an angle with respect to the proximal end 63 and extend around the entire periphery of a portion of exterior wall 68 to form a general frusto-conical gear teeth surface adjacent the proximal end 63. The outer-most external diameter 67 of gear member 16 is sized to be the same as or slightly smaller than the smallest outer diameter of endplates 20, 40. In this regard, when prosthetic device 10 is viewed from the end in a plane perpendicular to longitudinal axis 18, as shown in FIG. 6, gear member 16 does not protrude radially outward from beyond the perimeter of endplates 20, 40. In one embodiment, the outer-most diameter of gear member 16 is substantially the same size as the smallest outer diameter of endplates 20, 40. As shown in FIG. 7, in one embodiment gear teeth 66 extend a width 69 in a generally radial direction and generally extend radially outward to the outer diameter of gear member 16. In this regard, teeth 66 may be designed to have a width 69 to accommodate the expected gear forces given the particular bevel gear ratio, types of material used, and desired overall inner diameter of prosthetic device 10. One skilled in the art will appreciate that the larger the outer diameter to which teeth 66 radially extend, the larger that teeth 66 may be designed while still maintaining the same gear ratio. In this regard, when teeth 66 are made larger, they generally have a better mechanical strength. Also, the ability to design larger, wider, and stronger teeth 66 is advantageous for embodiments wherein prosthesis 10 is made of PEEK, other plastic, or other non-metallic materials that may have less mechanical strength than, for instance, titanium. Furthermore, as described in one embodiment, because the outer-most diameter of gear member 16 may be as large as the smallest outer diameter of endplates 20, 40, and teeth 66 extend radially to the outer-most diameter of gear member 16, a larger inner diameter of gear member 16 may be manufactured without compromising mechanical gear strength. As a result, a larger overall inner diameter of prosthetic device 10 may be accommodated which allows the packing of more bone material therein and facilitates bone fusion once prosthetic 10 is implanted.

As seen in FIGS. 1 and 2, in one embodiment teeth 66 are substantially exposed to the exterior of prosthetic device 10. Because teeth 66 are exposed around the periphery, less material is needed to cover up the exposed teeth, which generally makes the prosthetic 10 lighter and easier to manufacture than prior art devices that require covering the gear teeth. In addition, the gear member 16 is more easily visible by a surgeon and more readily accessible by a rotation tool than devices that hide or cover gear teeth. As discussed in more detail below, such a feature allows, inter alia, a tool to engage teeth 66 at a multitude of angular positions around the periphery of outer member 14 to provide a surgeon with various surgical options for insertion of prosthetic device 10. Furthermore, the snap-on assembly feature of gear member 16 allows for the manufacture of thinner walled parts without sacrificing mechanical strength. As a result, prosthesis 10 is able to have a larger internal diameter which allows more space for bone-packing material.

Figure 10:
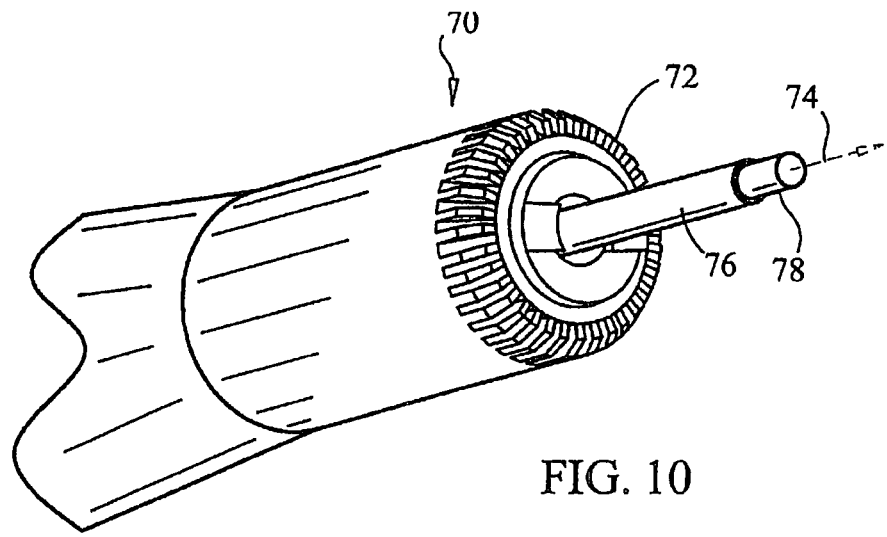
FIG. 10 is a perspective of one embodiment of a tool according to the present invention.
Figure 11:
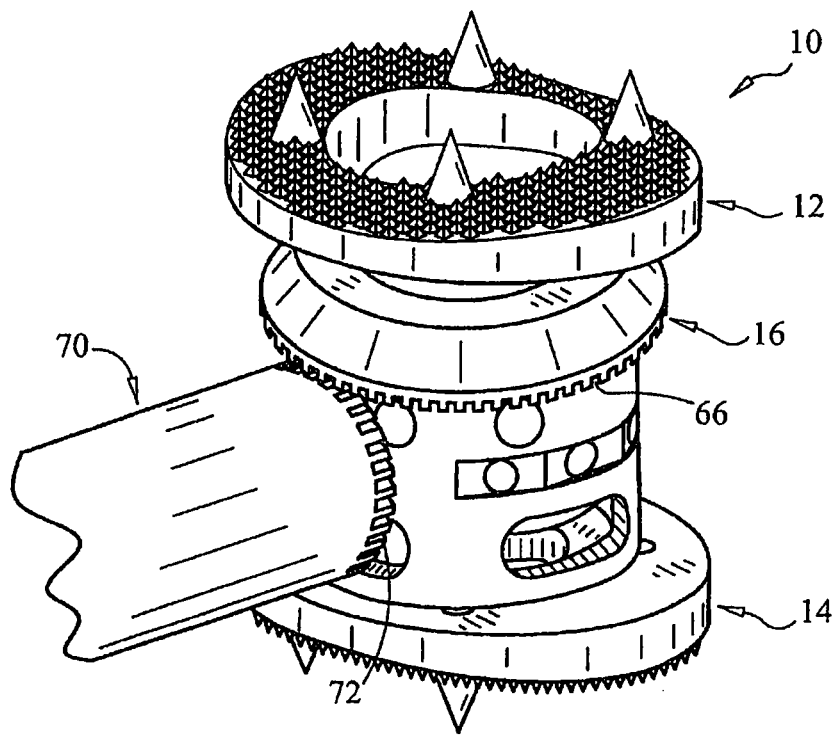
FIG. 11 is a perspective view of the tool of FIG. 10 shown engaging an embodiment of an expandable prosthetic device according to the invention.
Figure 12:
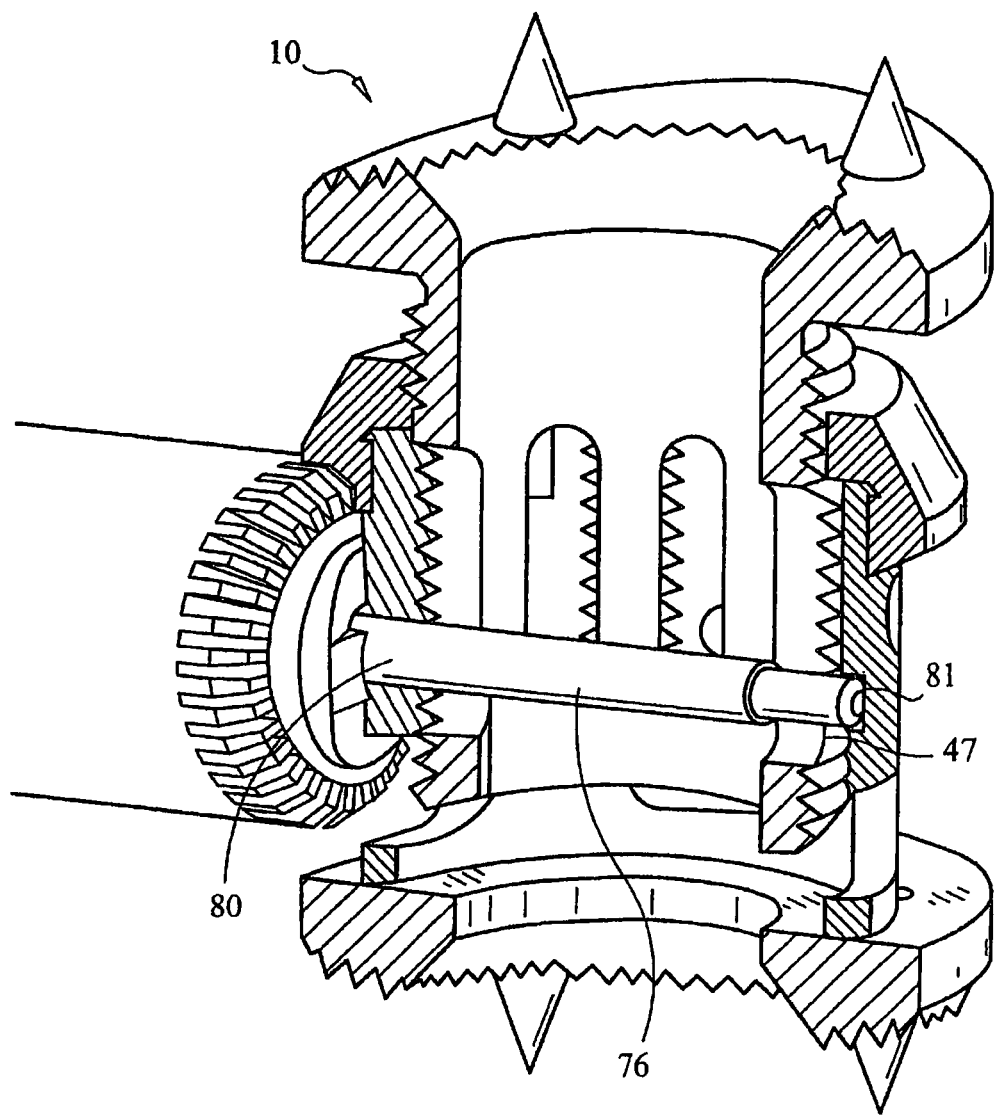
FIG. 12 is a partial cross-sectional view of the combination of FIG. 11.

As shown in FIGS. 10-12, prosthesis 10 may be expanded by a tool 70 that includes a bevel gear 72 at its distal end. Tool 70 extends along a tool axis 74 and in operation tool 70 is configured to engage prosthetic device 10 such that tool axis 74 is generally perpendicular to longitudinal axis 18. Bevel gear 72 is configured to engage teeth 66 of gear member 16 such that when bevel gear 72 is rotated about the axis of the tool, gear member 16 of prosthetic 10 is rotated about longitudinal axis 18 and inner member 12 translates along longitudinal axis 18 to expand prosthesis 10. In one embodiment, tool 70 may include a central shaft 76 having a threaded distal tip portion 78 that extends distally beyond bevel gear 72 to facilitate location and mounting of tool 70 with prosthetic 10. Threaded distal tip portion 78 may be configured to extend radially through a tool location hole 80 in outer member 14 and threadedly engage a threaded hole 81 located on the inner surface 48 of wall 47 positioned diametrically opposite hole 80 to fix the central shaft 76 of tool 70 to outer member 14. Once central shaft 76 is fixed to outer member 14, bevel gear 72 may rotate with respect to central shaft 76 to effect rotation of gear member 16 and translation of inner member 12.

Referring again to FIGS. 2 and 4, in one embodiment of prosthetic device 10 a plurality of mounting features or tool location holes 80, 82, 84 are provided along the outer surface 50 of outer member 14. Tool location holes 80, 82, 84 may be spaced around outer surface 50 in a predetermined arrangement to allow insertion of prosthetic device 10 utilizing different surgical approaches. For example, one skilled in the art will appreciate that holes 80, 82, 84 may be arranged to permit insertion through a lateral approach, anterolateral approach, or an anterior approach. As shown in FIG. 4, tool location hole 80 is angularly located or positioned on wall 47 toward the front of prosthetic 10 or toward the short end of end plates 20, 40 to facilitate insertion of prosthetic device 10 into a patient via an anterior approach. Tool location hole 82 may be angularly located or positioned on wall 47 to be toward the side of prosthetic 10 or toward the long end of end plates 20, 40 to facilitate insertion of prosthetic device 10 into a patient via a lateral approach. In addition, a third tool location hole 84 may be angularly located or positioned to be between location holes 80 and 82 to facilitate insertion of prosthetic device 10 through an anterolateral approach. As described previously, for each location hole 80, 82, 84, a corresponding threaded hole 81, 83, 85 may be formed on the inner surface 48 of wall 47 and positioned diametrically opposite the corresponding tool location hole to permit the threaded engagement of distal tip portion 78 of tool 70.

As best seen in FIGS. 1, 2 and 4, a locking member 120 may be provided to substantially restrict all relative movement between inner member 12 and outer member 14, when, for example, the desired expansion of the prosthetic device 10 has been obtained. In one embodiment of the locking member 120 according to the invention, a portion of locking member may protrude radially inward from the outer member 14 to engage the external surface 30 or thread 32 of inner member 12 and lock or fix inner member 12 to outer member 14 by friction and/or deformation of external threads 32. An internal locking screw 121 may be provided internal to locking member 120 to translate the locking member radially inward when the screw 121 is rotated. Screw 121 may be provided with a hexagonal head at its externally exposed end to facilitate engagement with an allen wrench or other tool to rotate screw 121 and drive locking member 120 radially inward to lock inner member 12 in place. In one embodiment, a plurality of locking members 120, 122, 124 may be provided spaced around the periphery of outer member 14 such that a surgeon can easily extend the locking member when utilizing any one of the aforementioned tool location holes 80, 82, 84.

Referring to FIGS. 1-9, one embodiment of end plates 20, 40 is shown wherein each end plate has a generally oblong or elliptical shape when viewed from the end or perpendicular to the longitudinal axis 18. As shown in FIG. 6, each end plate 20, 40 generally extends a width distance 90 (large outer diameter) along a long axis 92 in a medial-lateral direction and a length distance 94 (small outer diameter) along a short axis 96 in the anterior posterior direction, wherein width 90 is larger than the length 94. The oblong or elliptical shape of end plates 20, 40 is designed to resemble or mimic the footprint of the vertebral body to which the end plates will engage. In this regard, end plates 20, 40 are configured to engage portions of the vertebrae in a predetermined orientation, namely with long axis 92 extending in a medial-lateral direction, to maximize contact of the superior surface of the end plates 20, 40 with bone.

Figure 13:
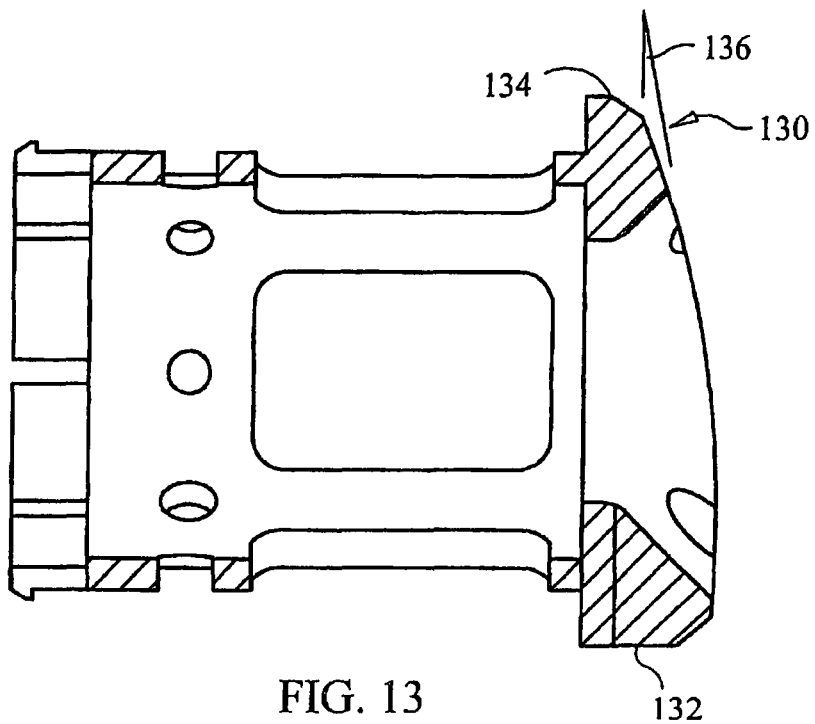
FIG. 13 is a cross-sectional view of another embodiment of an outer member according to the invention.

The dimensions of end plates 20, 40 can be varied to accommodate a patient's anatomy. Typically, end plates 20, 40 may have a width between about 14-32 mm (in the medial-lateral direction) and a length between about 12-25 mm (in the anterior-posterior direction). In some embodiments, implants 20, 40 have a wedge-shaped profile to accommodate the natural curvature of the spine. For example, as shown in FIG. 13, one embodiment of a wedge shape is shown wherein the end plate 130 has a gradual decrease in height from an anterior side 132 to a posterior side 134. In anatomical terms, the natural curvature of the lumbar spine is referred to as lordosis. When prosthetic device 10 is to be used in the lumbar region, the angle 136 formed by the wedge should be approximately between 4 degrees and 16 degrees so that the wedge shape is a lordotic shape which mimics the anatomy of the lumbar spine. In alternate embodiments, the wedge shape profile may result from a gradual increase in height from anterior side 132 to posterior side 134 to mimic the natural curvature in other regions of the spine. Thus, in other embodiments, angle 136 may be between about −4 degrees and −16 degrees.

As shown in FIGS. 1 and 2, a plurality of mounting holes 98 are spaced around the perimeter of each end plate 20, 40 for receiving insertable bone engaging members 100. In one embodiment, bone engaging members 100, comprise conical spikes 102 each having a cylindrical base portion 104 configured to fit within holes 98, for instance by press-fit. In alternate embodiments, differently shaped bone engaging members 100 may be used, or in other embodiments no bone engaging members may be used. Referring again to FIG. 2, according to one embodiment, end plates 20, 40 have chamfered edges 106 around the perimeter to facilitate insertion and/or accommodate the shape of the vertebral bodies which they engage. The superior or bone engaging surface 108 of endplates 20, 40 may also include numerous types of texturing to provide better initial stability and/or grasping contact between the end plate and the respective vertebrae.

The dimensions of prosthetic device 10 in accordance with the invention may be as follows, although the dimensions of the embodiments shown in the figures are not critical to the invention. In one embodiment, inner member 12 may have a total height 140 of between about 13-68 mm, outer member may have a total height 142 of between about 11-64 mm, and prosthetic device 10 may be extended to a total prosthetic height of between about 15-130 mm, depending on the configuration and desired application.

In alternate embodiments, the length, diameter, and shape of prosthetic device 10 may vary to accommodate different applications, different procedures, implantation into different regions of the spine, or size of vertebral body or bodies being replaced or repaired. For example, prosthetic device 10 may be expandable to a longer distance to replace multiple vertebral bodies. Also end plates 20, 40 can be sized and shaped to accommodate different procedures. For example, end plates 20, 40 may be made smaller for smaller statured patients or for smaller regions of the cervical spine. In addition, it is not required that end plates 20, 40 be shaped and sized identically and in alternate embodiments they can be shaped or sized differently than each other and/or include different bone engaging members or texturing.

Figure 14:
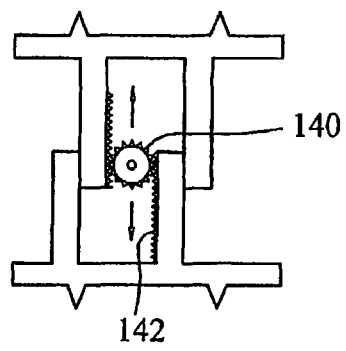
FIGS. 14-25 depict various alternate embodiments of expandable prosthetic devices according to the present invention.
Figure 15:
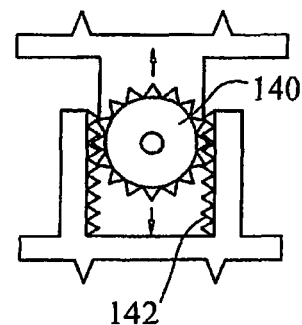
Figure 16:
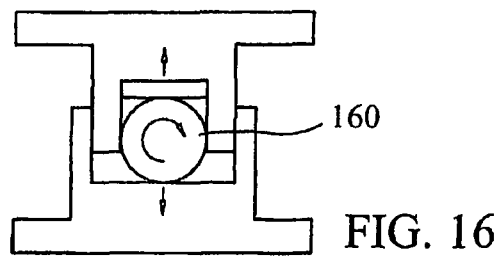
Figure 17:
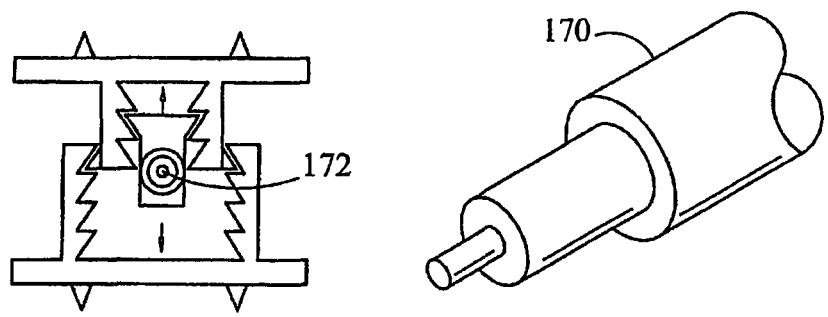
Figure 18:
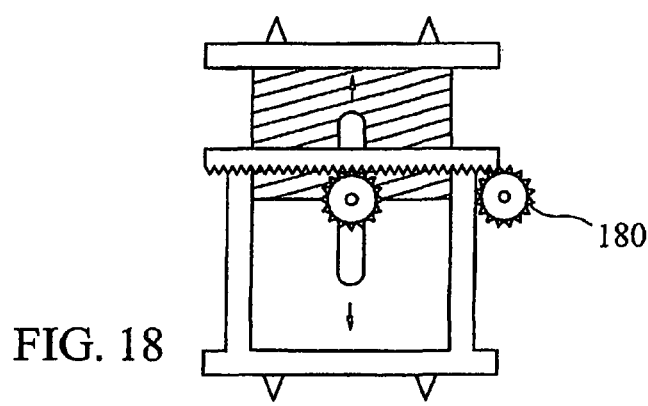
Figure 19:
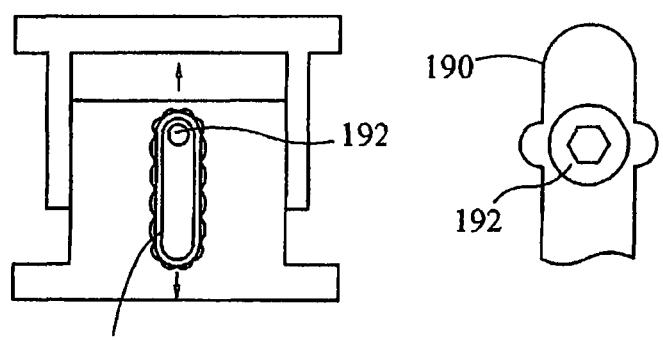
Figure 20:
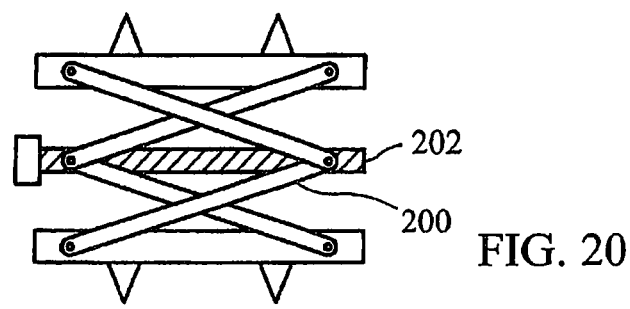
Figure 22:
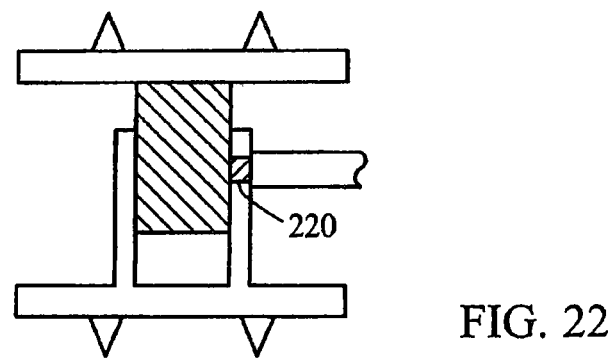
Figure 23:
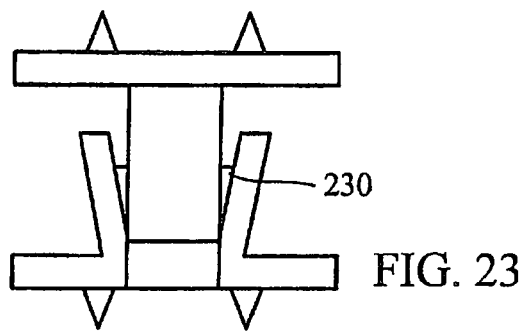
Figure 24:
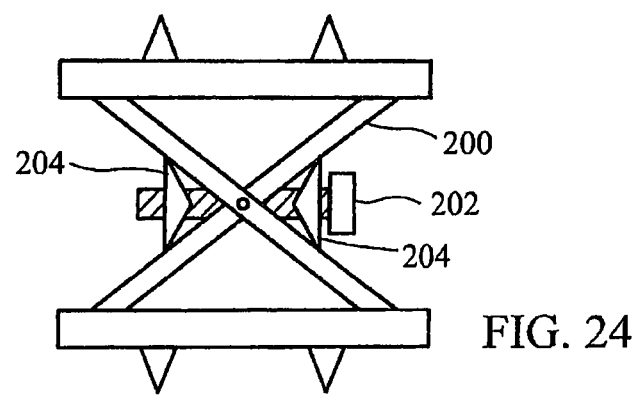

Referring to FIGS. 14-25, various alternate embodiments of expandable prosthetic devices according to the present invention are shown. Referring to FIGS. 14 and 15, in one variation a central gear member 140 may be positioned between the inner and outer members to engage teeth 142 to facilitate expansion. Referring to FIG. 16, in another embodiment an oblong cam 160 may be used to facilitate expansion. As shown in FIG. 17, an eccentric driver 170 may be used to mate with an oblong hole 172 to provide expansion. As shown in FIG. 18, in another embodiment an alternate worm gear 180 can be used. Referring to FIG. 19, a slot 190 with a cam lock 192 may be used to expand and lock the device at a certain expansion distance. Referring to FIGS. 20 and 24, in other embodiments, a scissor jack 200 and threaded screw 202 may be used to facilitate expansion.

Figure 21:
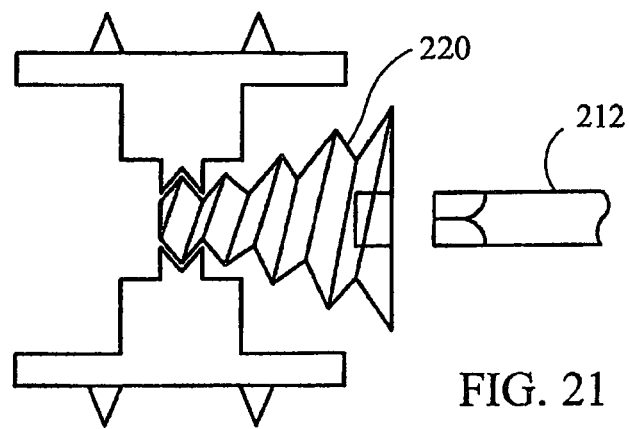
Figure 25:
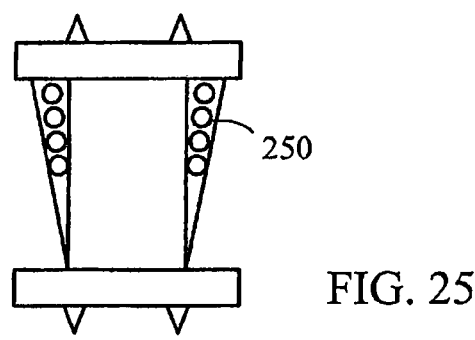

As shown in FIG. 24, a wedge 204 may be used to engage the scissor jack 200. Referring to FIGS. 21 and 22, alternate threaded devices may be used to expand the prosthetic device. As shown in FIG. 21, a tapered screw 210 may be used that may be driven by a driver 212. Alternatively, as shown in FIG. 22, a simple screw threaded engagement between the inner member and outer member may used. Also a set screw 220 may be used to lock the device at a certain expansion distance. Referring to FIGS. 23 and 25, the inner and outer members may be shaped to ride along an inclined plane or ramp. As shown in FIG. 23, a locking wedge or ring 230 may be provided to lock the device at a certain expansion distance. As shown in FIG. 25, rollers 250 may be provided to facilitate expansion of the device.

Figure 26:
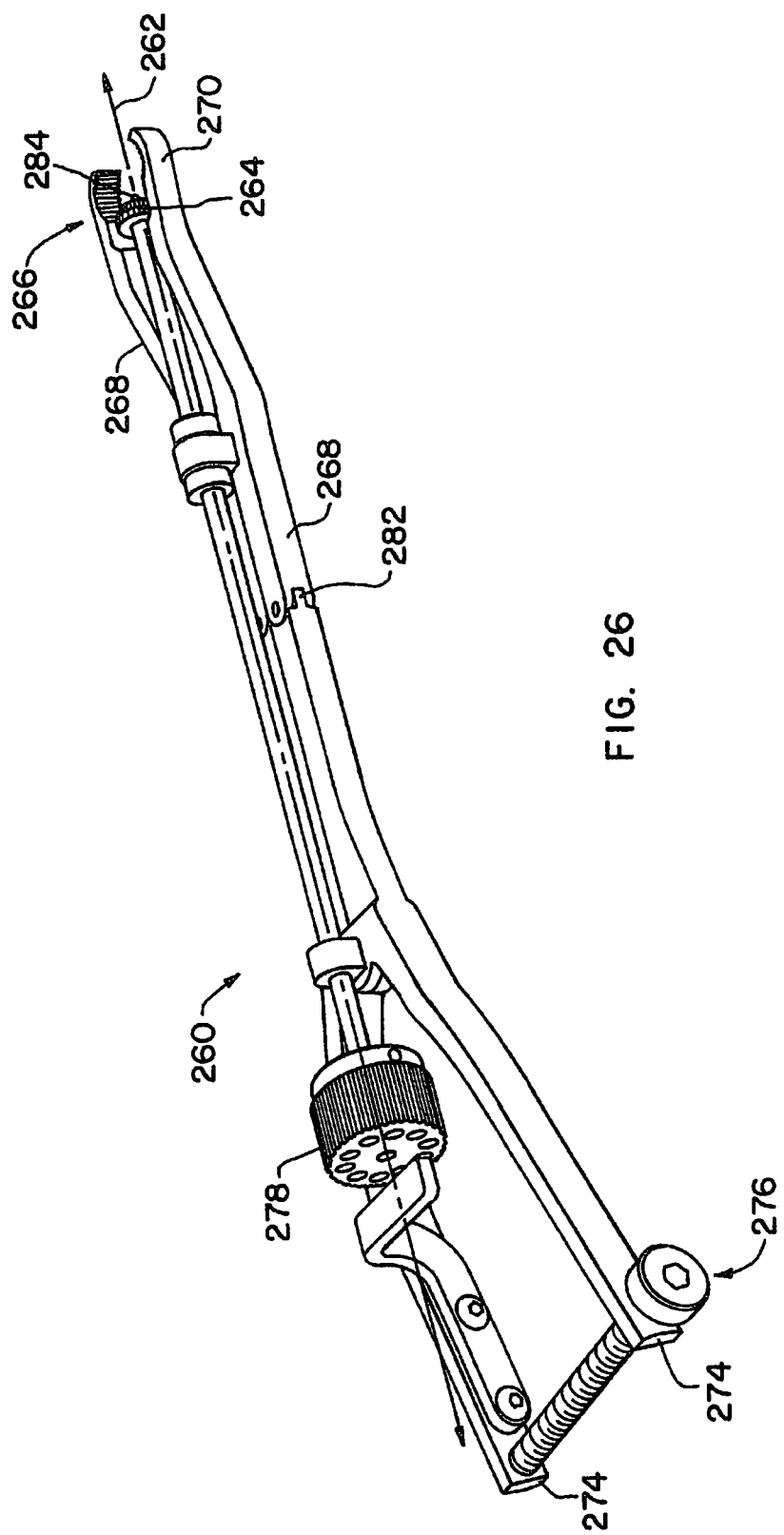
FIG. 26 is a perspective view of one embodiment of another tool constructed according to the invention.
Figure 27:
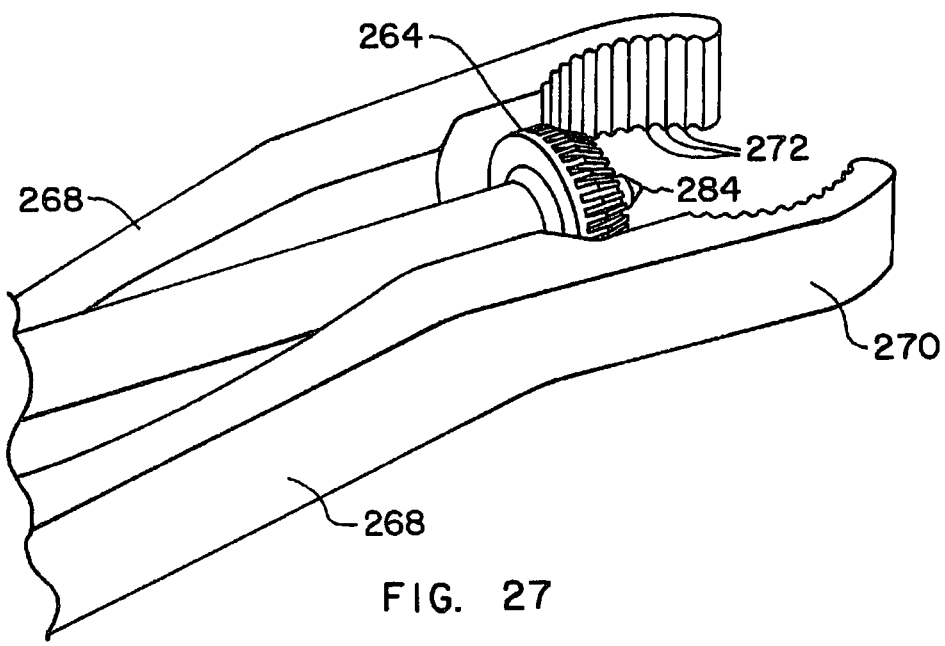
FIG. 27 is an enlarged view of a portion of the tool of FIG. 26.

Referring to FIGS. 26-27, another embodiment of a holder or tool 260 is shown that may be used to hold, insert, and/or expand a prosthesis of the invention. Tool 260 extends along a longitudinal or tool axis 262 and includes a bevel gear 264 adjacent its distal end 266. Tool 260 comprises arms 268 extending longitudinally along axis 262 and defining a claw or clamping portion 270 adjacent distal end 266. As described above with respect to tool 70, bevel gear 264 is configured to engage teeth 66 of gear member 16 to expand prosthesis 10. In this embodiment, clamping portions 270 of arms 268 are configured to engage the lateral sides or exterior central portion of prosthesis 10 to clamp and/or hold prosthesis 10 therebetween while allowing bevel gear 264 to rotate and expand prosthesis 10. As best seen in FIG. 27, in one embodiment, clamping portions 270 may include teeth or bevels 272 configured generally to facilitate or enhance the grip or purchase of a prosthesis between the clamping portions 270 of arms 268. As shown in FIG. 26, arms 268 may be actuated by compressing proximal ends 274. In this regard, a hinge 282 may be provided intermediate the length of arms 268 which causes clamp portions 270 to compress inward when proximal ends 274 of arms 268 are compressed inwards. In one embodiment, proximal ends 274 may be threadedly interconnected and may be actuated by advancing or rotating a screw 276. In operation, the threaded portion of screw 276 mechanically aids in the physical clamping or holding force applied on prosthesis 10 by clamping portions 270. One skilled in the art will appreciate that a surgeon's hands may be freed to perform other tasks while being assured that a secure hold of prosthesis 10 by tool 260.

Figure 29:
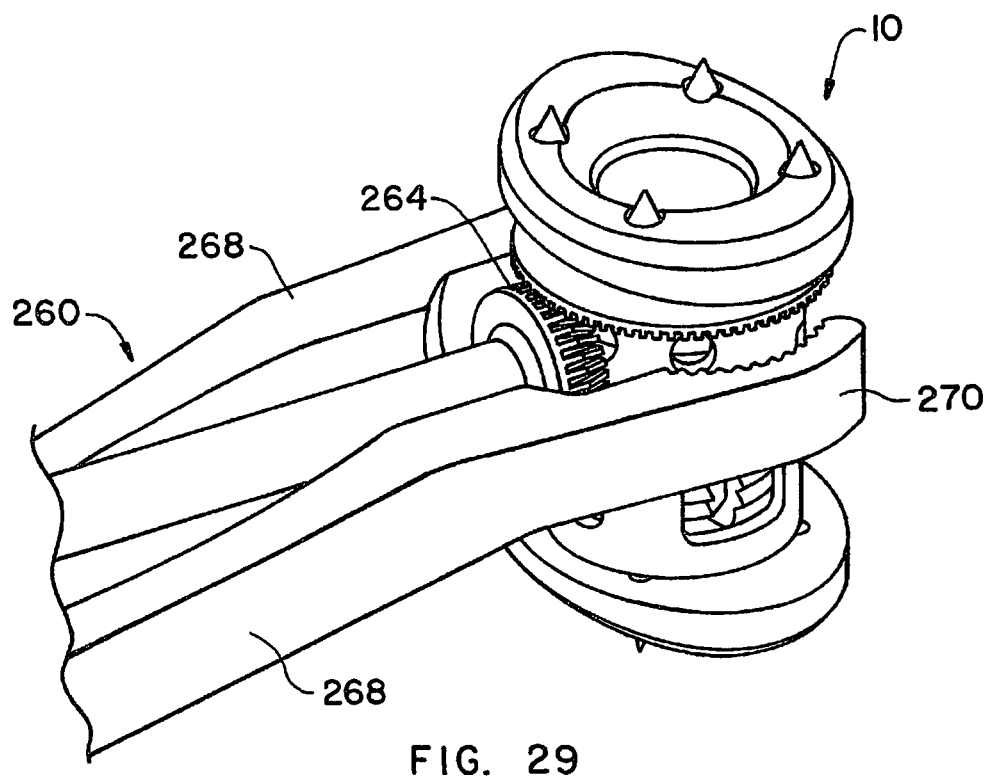
FIG. 29 is an enlarged view of a portion of the assembly of FIG. 28.
Figure 28:
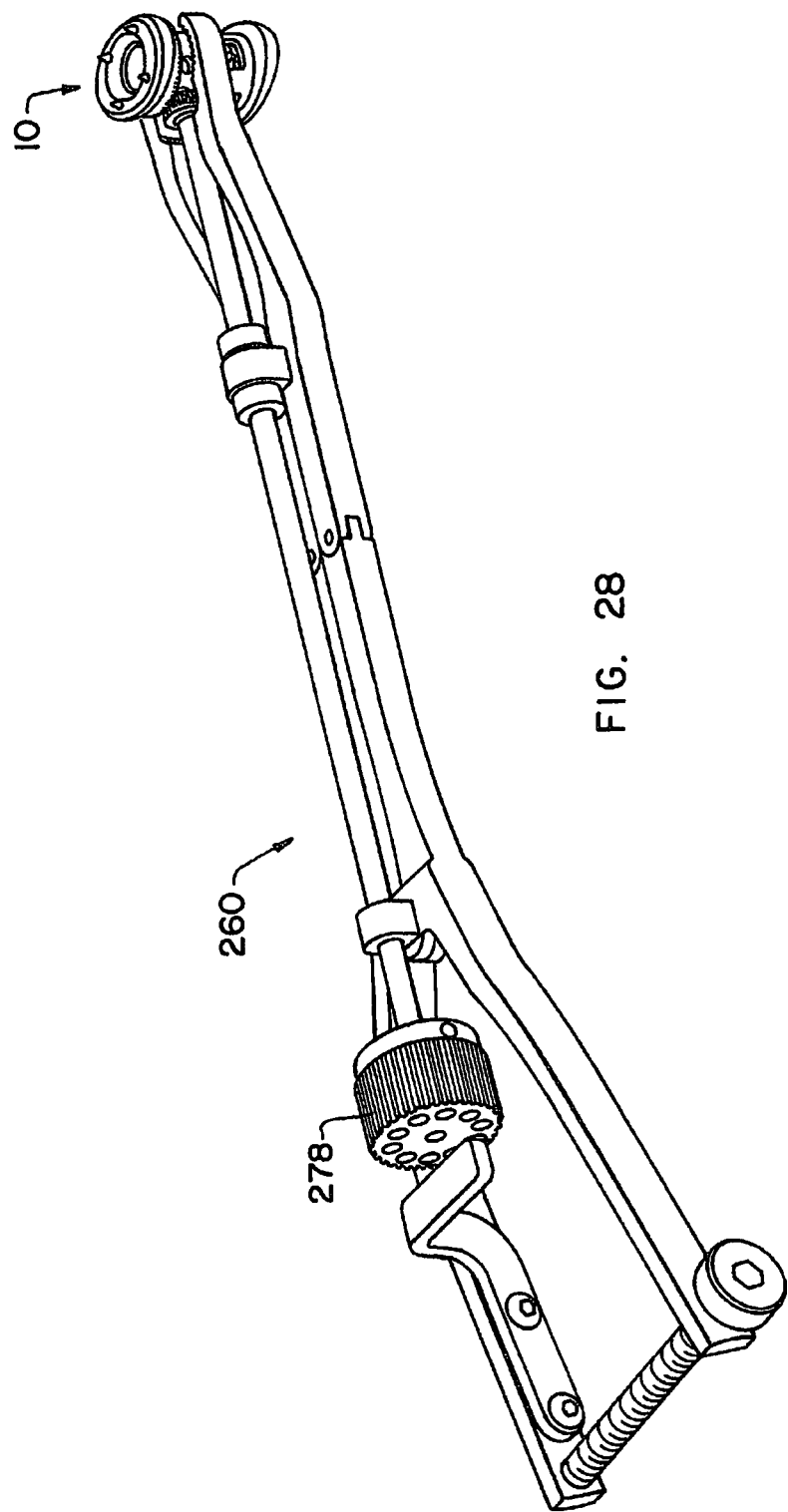
FIG. 28 is a perspective view of one embodiment of an assembly of the tool of FIG. 26 with one embodiment of an expandable prosthetic device according to the invention.

Bevel gear 264 may be rotated by dial 278 positioned adjacent a proximal end of shaft 280. In this regard, a surgeon may actuate or expand prosthesis 10 remote from the prosthesis, i.e. outside of a patient's body during implantation. In one embodiment, centering or positioning pin 284 extends distally from bevel gear 264 and is configured and dimensional to engage an opening in prosthesis to locate bevel gear 264 adjacent gear member 16 of prothetic 10. Referring to FIGS. 28-29, perspective views of tool 260 assembled to a prosthetic 10 are shown.

Figure 30:
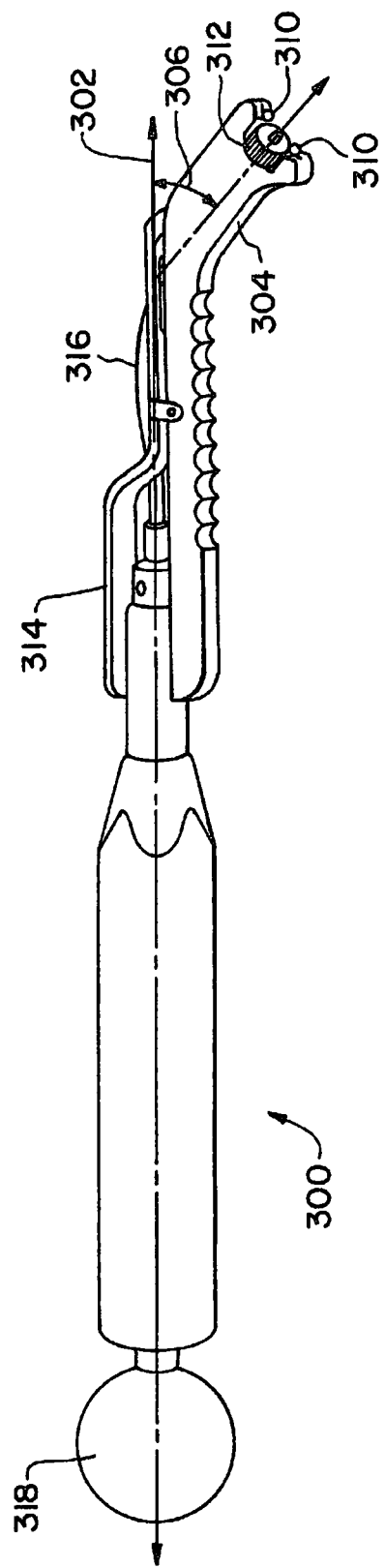
FIG. 30 is a perspective view of another embodiment of a tool according to the invention.

Referring to FIG. 30, another embodiment of a holder or tool 300 is shown that may be used to hold, insert, and/or expand a prosthesis of the invention. According to this embodiment, tool 300 is configured to be used with prosthesis 10 utilizing a transforaminal approach. In this regard, tool 300 is configured and dimensional to engage or hold prosthesis 10 at an angle with respect to tool axis 302.

According to one embodiment, tool 300 extends along a longitudinal or tool axis 302 and generally comprises an angled distal end portion 304 extending at an angle 306 with respect axis 302. In one embodiment, angle 306 is between about 30 and about 60 degrees. In another embodiment, angle 306 is about 45 degrees. Distal tip 308 of end 304 may comprise prongs 310 extending distally on either side of bevel gear 312. Prongs 310 are configured and dimensioned to engage openings in prosthesis 10 to locate bevel gear 312 adjacent gear member 16 of prosthetic 10. In this embodiment, prongs 310 may be extendable in the distal direction from portion 304 to hold or grip prosthetic 10. In one variation, a compressible handle 314 may be provided to actuate prongs 310 in an outward or distal direction to contact, engage, or hold prosthesis 10 at a distal end of tool 300. A flexible shaft 316 may extend the length of tool 300 from rotation sphere 318 to bevel gear 312, such that bevel gear 312 may be rotated upon rotation of sphere 318. As with previously described embodiments, a surgeon may actuate or expand a prosthesis 10 remote from the prosthesis or outside the patient's body during implantation. Handle 314 may be released to cause prongs 310 to retract and release prosthesis 10 once the prosthesis is implanted.

Figure 31:
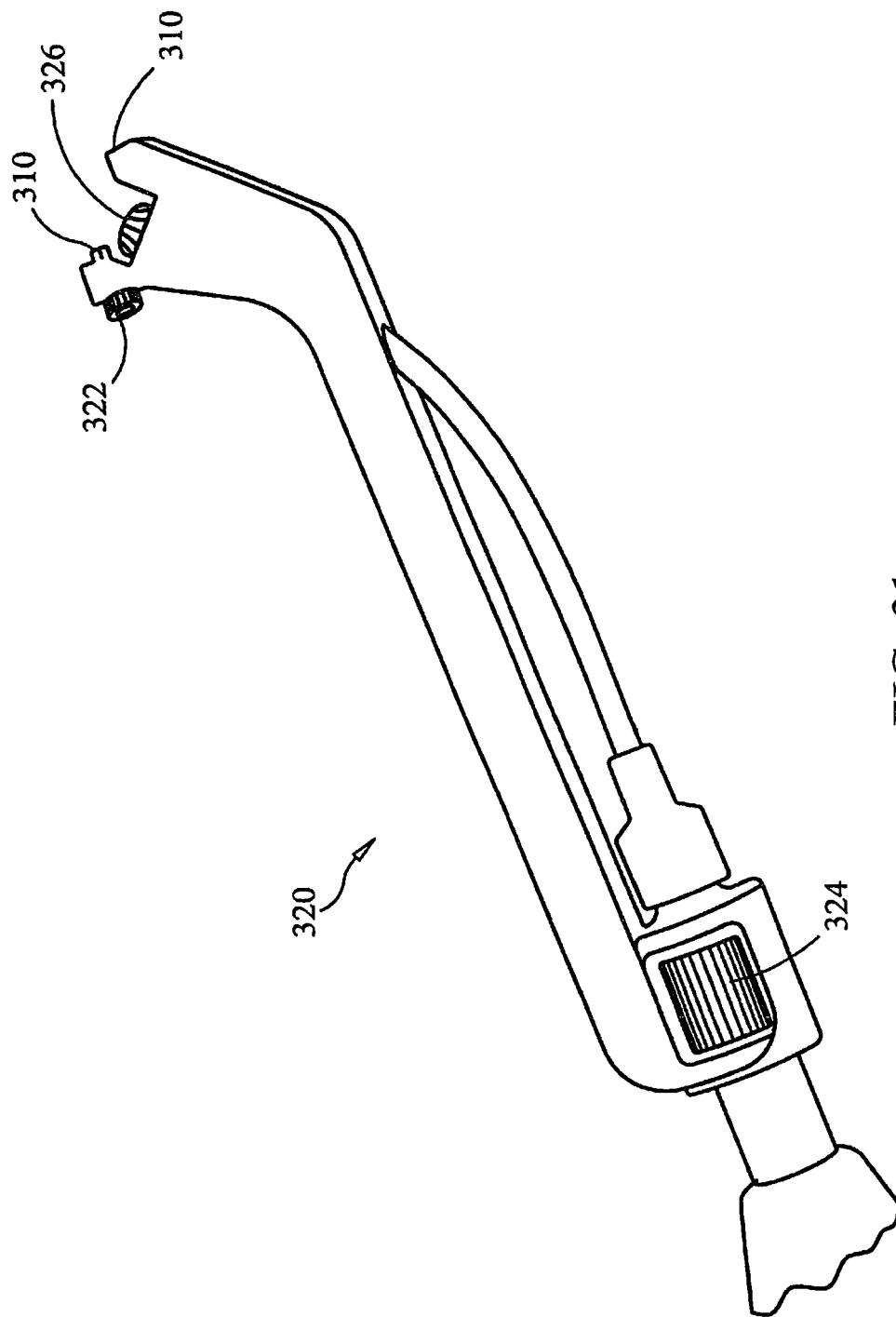
FIG. 31 is a perspective view of another embodiment of a tool according to the invention.
Figure 32:
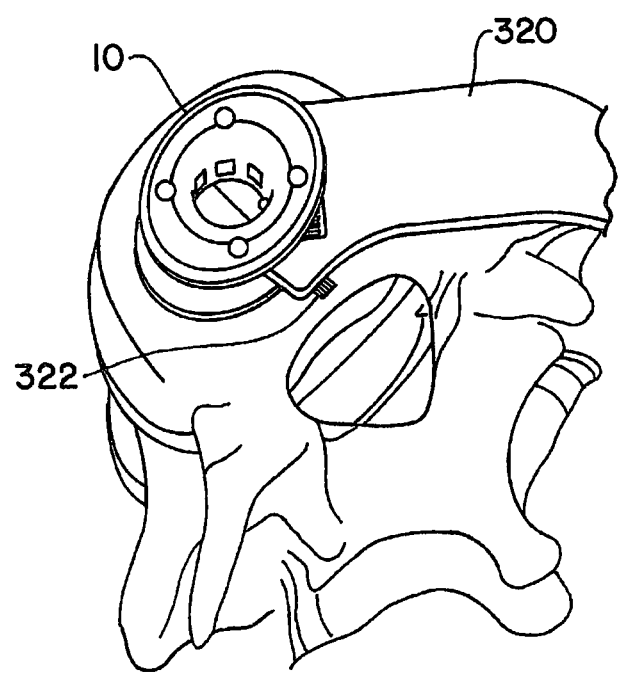
FIG. 32 is a perspective view of the tool of FIG. 31 shown adjacent a portion of a spine.

Referring to FIGS. 31 and 32, another embodiment of a holder or tool 320 is shown. Tool 320 is similar to tool 300 except prongs 310 are not actuatable by a compressible handle, as described above. In this embodiment, a set screw 322 is provided to threadedly engage prosthesis 10 to fixedly hold or secure prosthesis 10 with respect to tool 320. According to one embodiment, tool 320 may also include an alternate rotating mechanism, such as rotating dial 324, to rotate the bevel gear 326 positioned at the distal tip of the tool. Referring to FIG. 32, an assembly view of tool 320 with prosthesis 10 attached thereto is shown. As with tool 300, tool 320 is configured and dimensioned to insert, engage, or hold prosthesis 10 at an angle with respect to the longitudinal axis of the tool and is generally configured to be implanted using a transforaminal approach, as shown in FIG. 32. Once implanted, a surgeon can loosen screw 322 to release prosthesis 10

Figure 33:
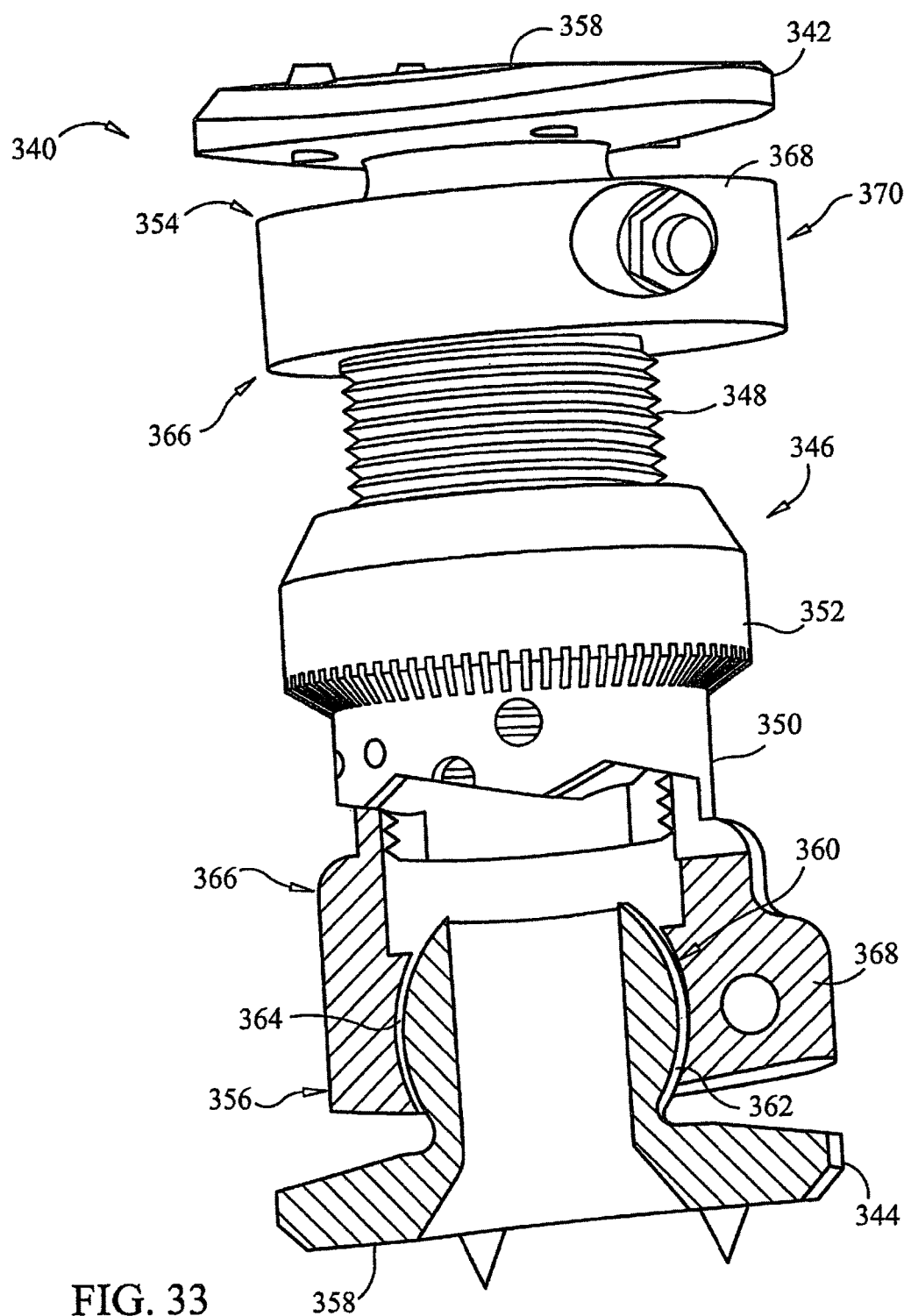
FIG. 33 is a perspective view of another embodiment of an expandable prosthetic device according to the invention.

Referring now to FIG. 33, an alternate embodiment of an expandable vertebral prosthesis device 340 is shown. Prosthesis 340 is generally similar to prosthesis 10 with the exception that the endplates 342, 344 are rotatably and pivotably connected to the body 346 of prosthesis 340. In this embodiment, endplates 342, 344 are rotatable and/or pivotable about multiple axes. As such, endplates 342, 344 are multi-axially connected to body 346 of prosthesis 340. In one embodiment, endplates 342, 344 are selectably fixable at any desired pivot angle or rotation position. As with the embodiments disclosed above, prosthesis 340 generally comprises an inner member 348 telescopingly received within an outer member 350 and a gear member 352 generally configured to effect translation of inner member 348 with respect to outer member 350 and cause expansion of prosthesis 340. A first endplate 342 is connected to distal end 354 of inner member 348 and second endplate 344 is connected to a proximal end 356 of outer member 350. According to one embodiment, endplates 342, 344 generally comprise a generally flat outer or bone engaging surface 358 and an opposite connecting or articulating portion 360. Outer surface 358 is generally configured and dimensioned to contact or engage a bone surface, such as a portion of a vertebral body. According to one embodiment, articulating portion 360 has a generally spherical or ball shaped exterior 362 and is configured to articulate within or engage a correspondingly shaped socket 364 and facilitates rotational and/or pivotal articulation or movement therein. According to one embodiment, socket 364 may be defined within a clamping member 366 so that endplates 342, 344 may be selectably fixed at any position with respect to socket 364 when so desired by a user or surgeon. As seen in FIG. 33, in one embodiment, clamping member 366 generally comprises a C-shaped ring or body 368 with an opening 370 extending through a portion of the perimeter to allow the ring or body 368 to contract along its perimeter and thereby tighten, clamp or otherwise fix the articulating portion 360 of the endplates in position with respect to socket 364. In this regard a clamping screw (not shown) may extend across opening 370 and may be rotated to cause clamping member 366 to compress or clamp down on articulating portion 360. As one skilled in the art can appreciate, such a selectable positioning feature of endplates 342, 344 facilitates the accommodation of a wide variety of anatomical possibilities when prosthesis 340 is implanted. For example, a surgeon could pivot endplates 342, 344 to accommodate a wide range of lordotic angles of vertebral bodies.

Figure 34:
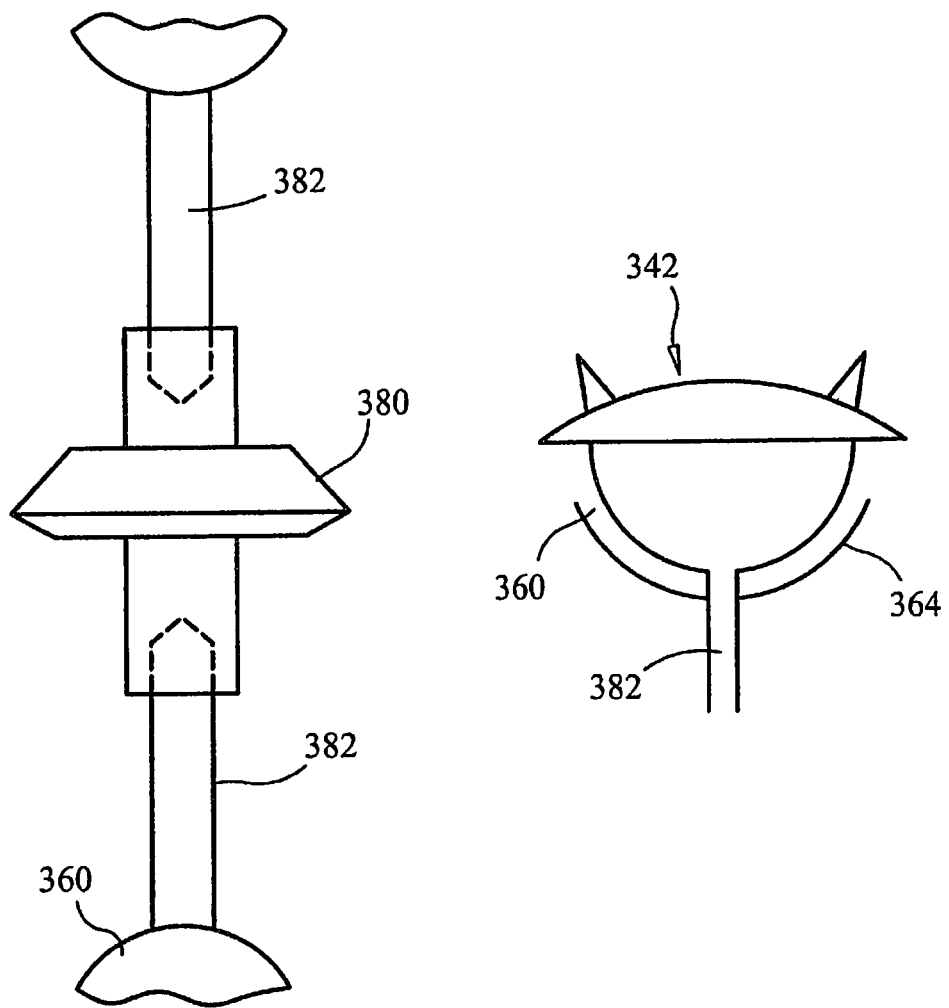
FIG. 34 is a side view of another embodiment of an expandable prosthetic device according to the invention.
Figure 35:
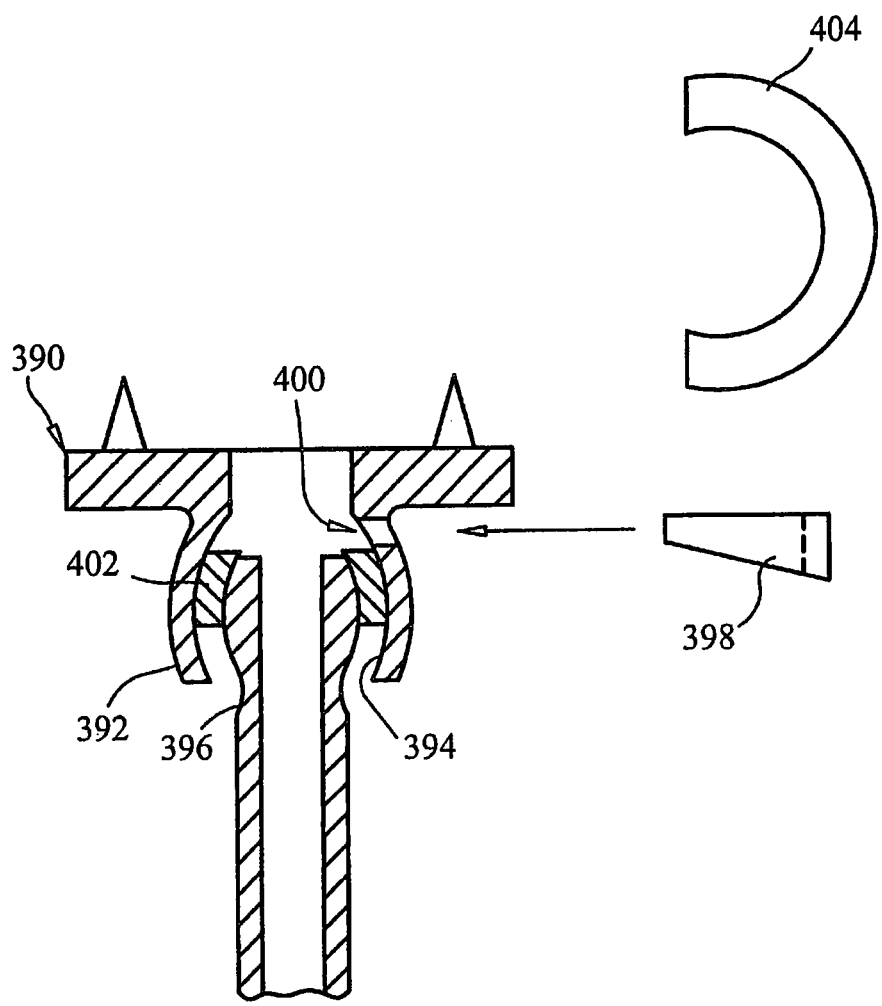
FIG. 35 is a partial cross-sectional view of another embodiment of an expandable prosthetic device according to the invention.

Referring to FIG. 34, an alternative locking mechanism may be provided to selectably lock endplates 342, 344 in place. In one variation, endplates 342,344 may be interconnected to gear member 380 by a cable 382 or the like. As ring gear 380 is rotated, a tension is applied on cables 382 pulling end plates 342, 344 closer together to bias articulating portion 360 against a contact surface of socket 364, thereby preventing further actuation of endplates 342, 344. Referring to FIG. 35, an alternative embodiment of a fixably actuatable endplate attachment mechanism is shown having an alternate locking mechanism. According to this embodiment, articulating portion 392 of endplate 390 comprises a spherical socket portion 394 configured to fit, engage or articulate with respect to a correspondingly shaped ball or spherical portion 396 to facilitate multi-axial rotation and/or pivoting articulation of endplate 390 with respect to spherical portion 396 in much the same manner described above. A ramped clip or wedge 398 may be inserted into a lateral opening 400 of endplate 390 to effect clamping, locking, or fixation of articulating portion 392 of endplate 390 with respect to spherical portion 396. In this regard, a collet 402 may be interposed between socket portion 394 and spherical portion 396 and when wedge 398 is advanced radially into endplate 390, collet 402 is compressed downward against socket 394 and spherical portion 396 to prevent further articulation. In one variation, wedge 398 has a partial annular, partial ring, or C-shaped body 404 with a ramped profile when viewed from the side.

Figure 36:
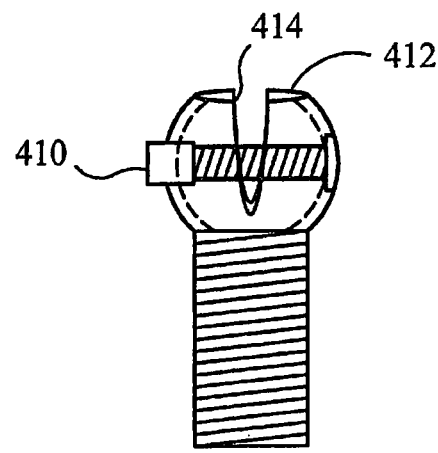
FIG. 36 is a partial perspective view of another embodiment of an expandable prosthetic device according to the invention.
Figure 37:
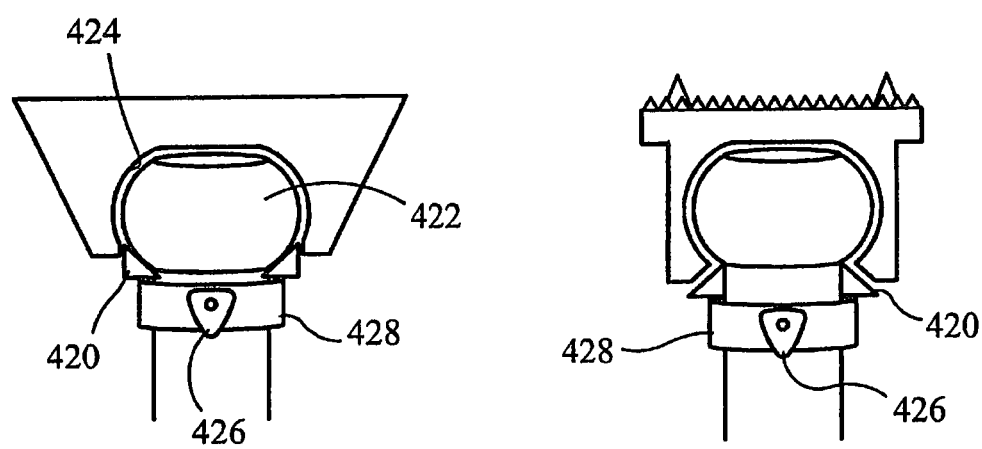
FIG. 37 is a partial side view of another embodiment of an expandable prosthetic device according to the invention.

Referring to FIGS. 36-37 additional alternative locking mechanisms are shown for locking or fixing a multi-axial rotatable or pivotable endplate in position with respect to a body of a prosthesis. Referring to FIG. 36, according to one embodiment, an expansion set screw 410 may be provided to expand a spherical or ball portion 412 of the ball and socket joint to frictionally engage the socket portion and prevent further rotation between the ball and socket portions of the joint. In this regard, the ball portion 412 may include one or more vertical slits, openings or V-shaped grooves 414 or openings to allow ball portion 412 to expand radially outward when screw 410 is rotated. Referring to FIG. 37 an alternative fixation mechanism is shown wherein a tapered collet 420 extends between the ball portion 422 and socket portion 424 and may be advanced or wedged further between the ball and socket portions to bind the joint and prevent rotation. According to one embodiment, the collet 420 may be advanced by rotating a cam 426 to advance a collar 428 and engage the collet 420 and force or wedge collet 420 between the ball and socket portions 422, 424 and thereby lock or angularly fix the endplate with respect to the body portion of the prosthesis.

Figure 38:
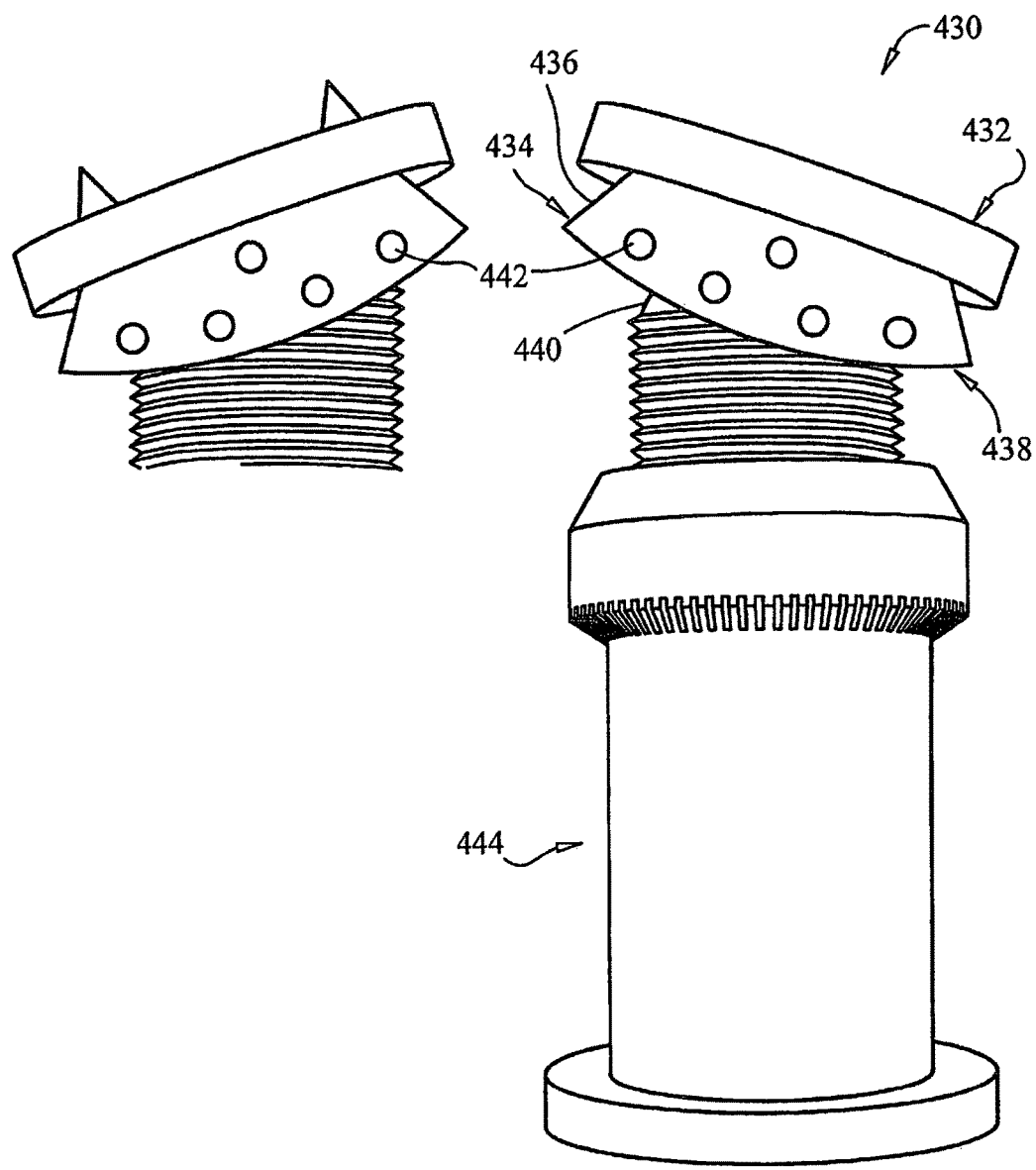
FIG. 38 is a perspective view of another embodiment of an expandable prosthetic device according to the invention.

Referring to FIG. 38, another embodiment of an expandable vertebral prosthesis device 430 having at least one fixable multi-axially rotatable endplate 432 is shown. Prosthesis 430 is generally similar to prosthesis 340, described above, with the exception that the endplate 432 may be fixed in selected angular positions utilizing a pin and skirt mechanism. According to one embodiment, articulating portion 434 of endplate 432 has a generally conical skirt member 436 defining a spherical socket or female portion 438 configured to engage a spherical or ball shaped portion 440 provided adjacent an end of prosthesis 430 and facilitates multi-axial rotational and/or pivotal movement thereabout. Skirt 436 may comprise a plurality of holes or openings 442 spaced about the perimeter of skirt 436 and extending therethrough to accommodate one or more pins (not shown) to fix or pin skirt 436 and endplate 432 with respect to prosthesis body 444. In this regard, a plurality of corresponding holes or openings (not shown) may be provided about ball portion 440 to receive one or more pins extending though openings 442 to fix endplate 432 with respect to prosthesis body 444.

Figure 39:
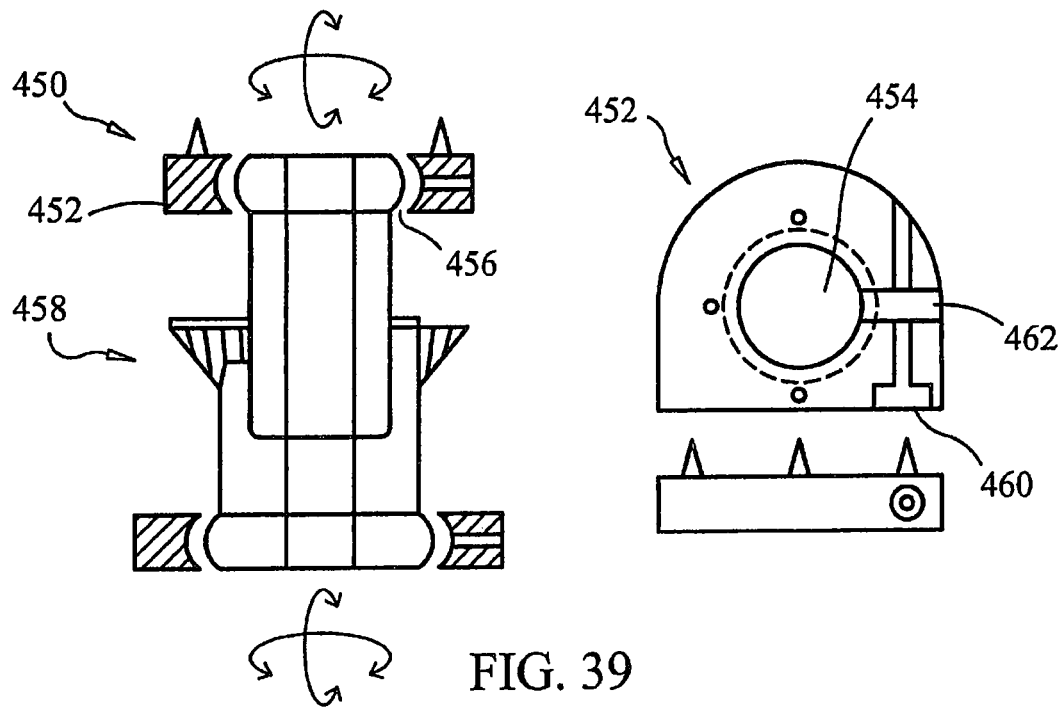
FIG. 39 is a cross-sectional view of another embodiment of an expandable prosthetic device according to the invention.

Referring to FIG. 39, an alternative embodiment of a prosthesis 450 is shown having an annular endplate 452 with a central opening 454 accommodating a partial spherical or ball shaped articulating portion 456 on the body 458 of prosthesis 450. A set screw 460 may be provided to clamp endplate 452 with respect to spherical portion 456. The set screw 460 may extend across a radially extending opening 462 in the perimeter of endplate 452 and generally functions similar to a C-clamp as explained above with respect to previously described embodiments.

Figure 40:
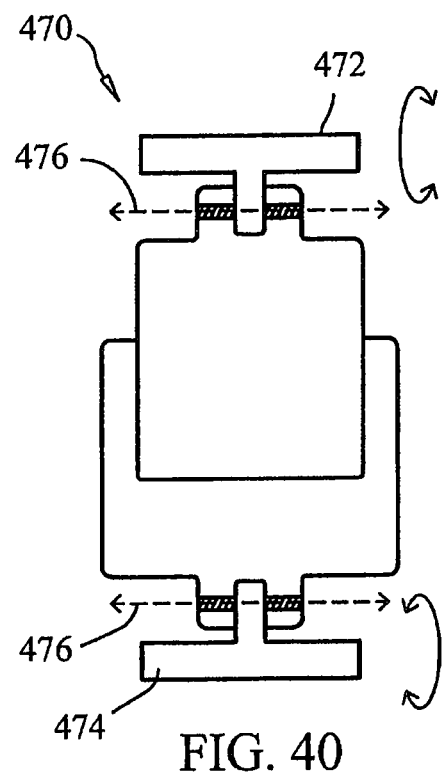
FIG. 40 is a cross-sectional view of another embodiment of an expandable prosthetic device according to the invention.

Referring to FIG. 40 an alternative embodiment of a prosthesis 470 is shown having a pivoting or articulating connection similar to a universal joint wherein the endplates 472, 474 are pivotable about a single axis 476. A set screw or other fixation device may be provided in a slotted hinge to facilitate selectable fixation or locking of the endplates at a desired orientation.

Figure 41:
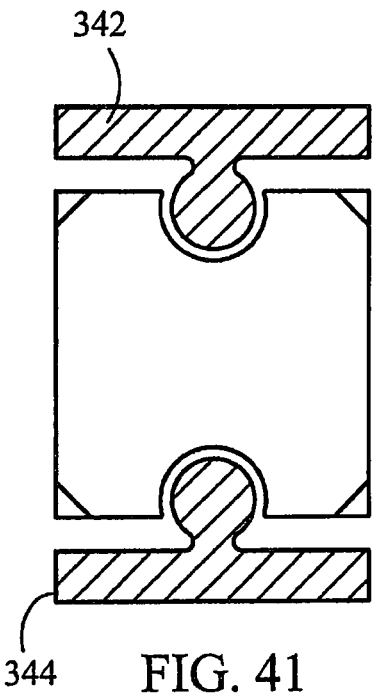
FIGS. 41-44 are partial cross-sectional views of additional embodiments of endplate connection mechanisms for expandable prosthetic devices according to the invention.
Figure 42:
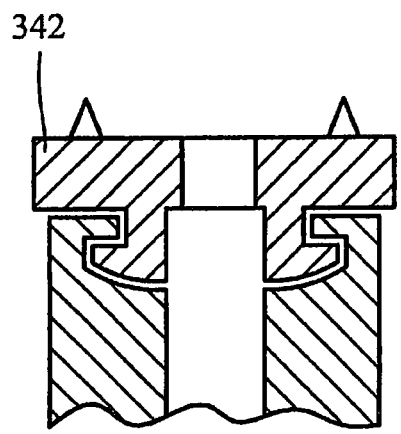
Figure 43:
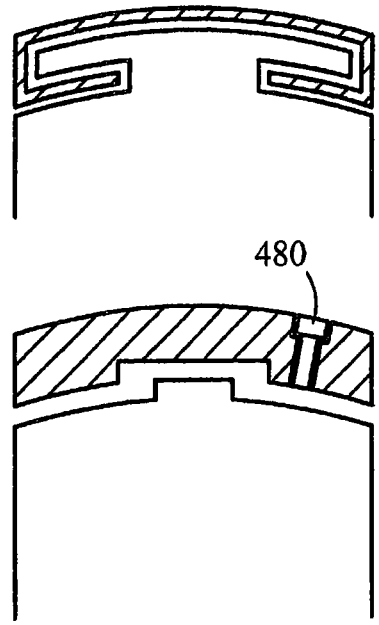
Figure 44:
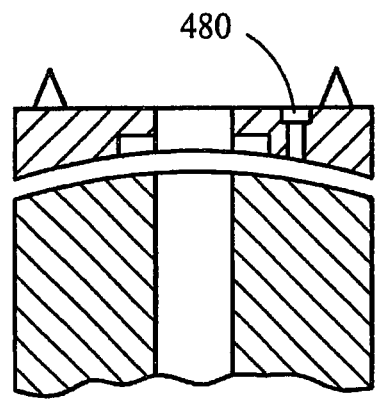

FIGS. 41-44 shows various alternative multi-axial coupling mechanisms that may be used to facilitate fixable angulation and/or rotation of endplates 342, 344 with respect to a body portion of an expandable prosthesis. Referring to FIG. 41, according to one embodiment, an endplate may be pivotable about a single axis with respect to the body of a prosthesis. Referring to FIG. 42, captured pivotal connections may be provided to prevent over-rotation of an endplate with respect to the body of a prosthesis. Similarly, in FIGS. 43-44 locking mechanisms such as a set screw 480 may be provided to prevent an endplate from rotating too far or over-rotating.

Figure 45:
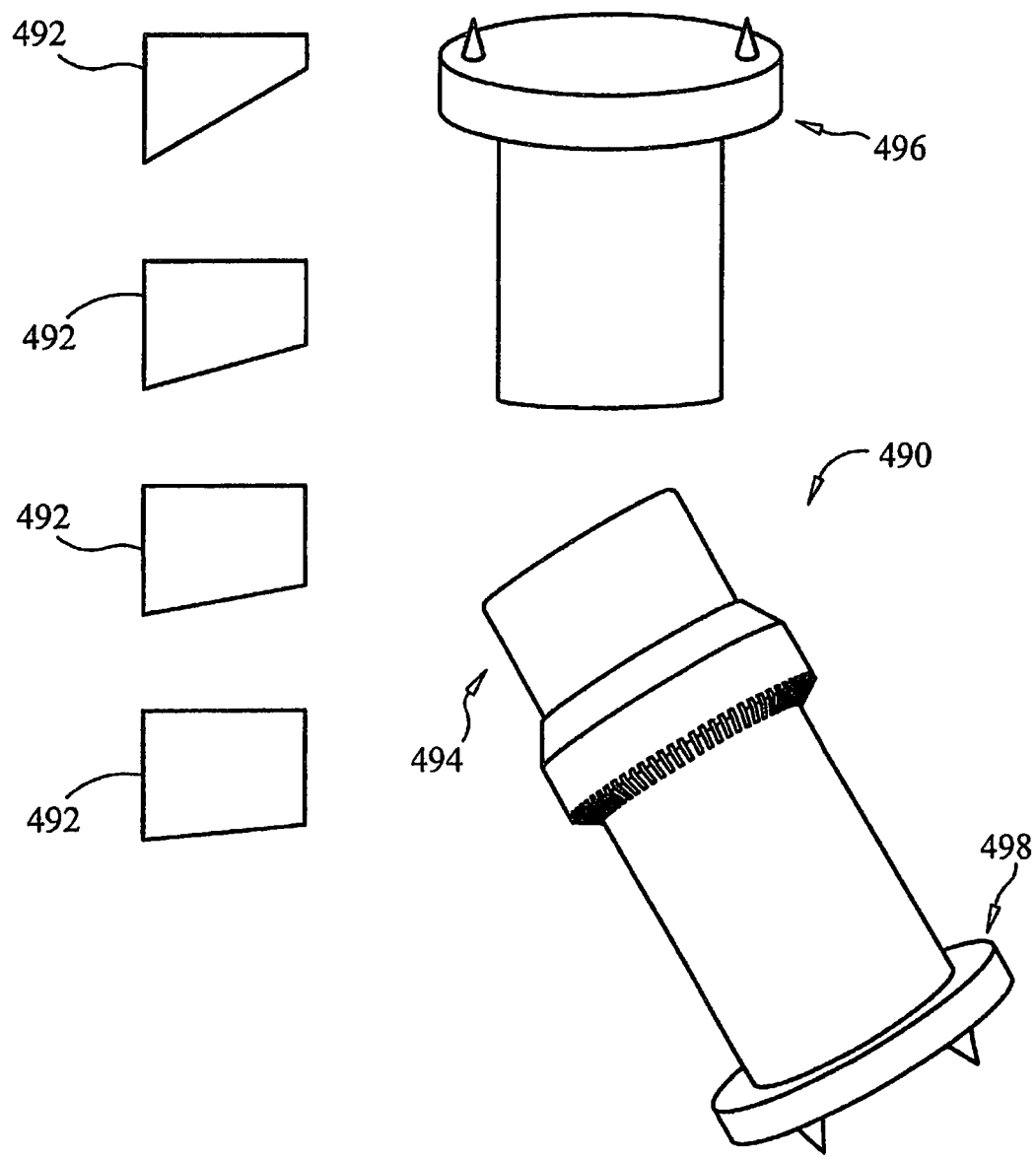
FIG. 45 is a perspective view of another embodiment of an expandable prosthetic device according to the invention.
Figure 46:
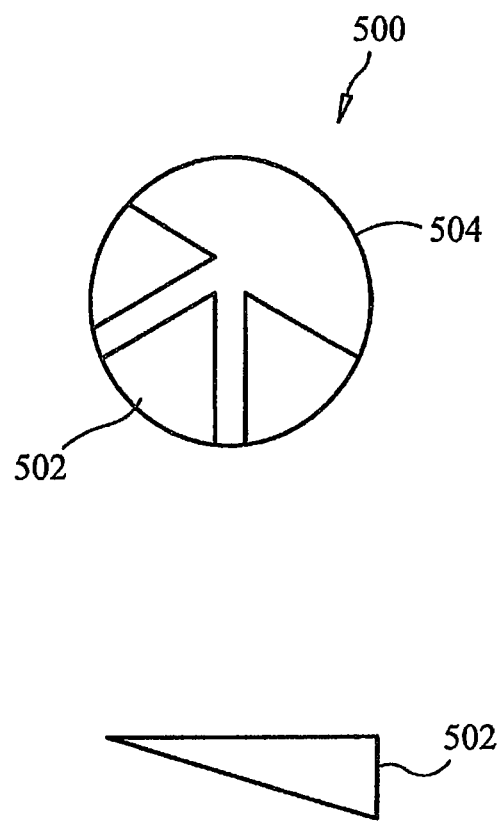
FIG. 46 is an end view of and endplate of another embodiment of an expandable prosthetic device according to the invention.

Referring to FIGS. 45 and 46, additional embodiments of expandable vertebral prosthetic devices 490, 500 are shown having endplates with selectable angular orientations. As shown in FIG. 45, prosthesis 490 may comprise modular insert members 492 having varying angular or wedge shapes. According to one exemplary embodiment, modular inserts 492 may have varying angles from between about 5 degrees to about 30 degrees. In this regard, when an angled insert member 492 is interposed into the body portion 494 of prosthesis 490 a variety of angular orientations of endplates 496, 498 may be obtained. In operation, a user or surgeon installing the prosthetic device may accommodate various lordotic angles. Referring to FIG. 46, in another embodiment, a plurality of triangular or pie shaped angular inserts 502 may be provided to be inserted directly into an endplate 504 to form the outer surface or bone engaging surface of an endplate. In this regard, a plurality angular inserts 502 may be provided with various angular shapes as desired. In operation, a user or surgeon may fashion an endplate having a desired contour utilizing any combination of modular angular inserts to, for example, accommodate a particular lordotic angle when the prosthesis is inserted.

Figure 47:
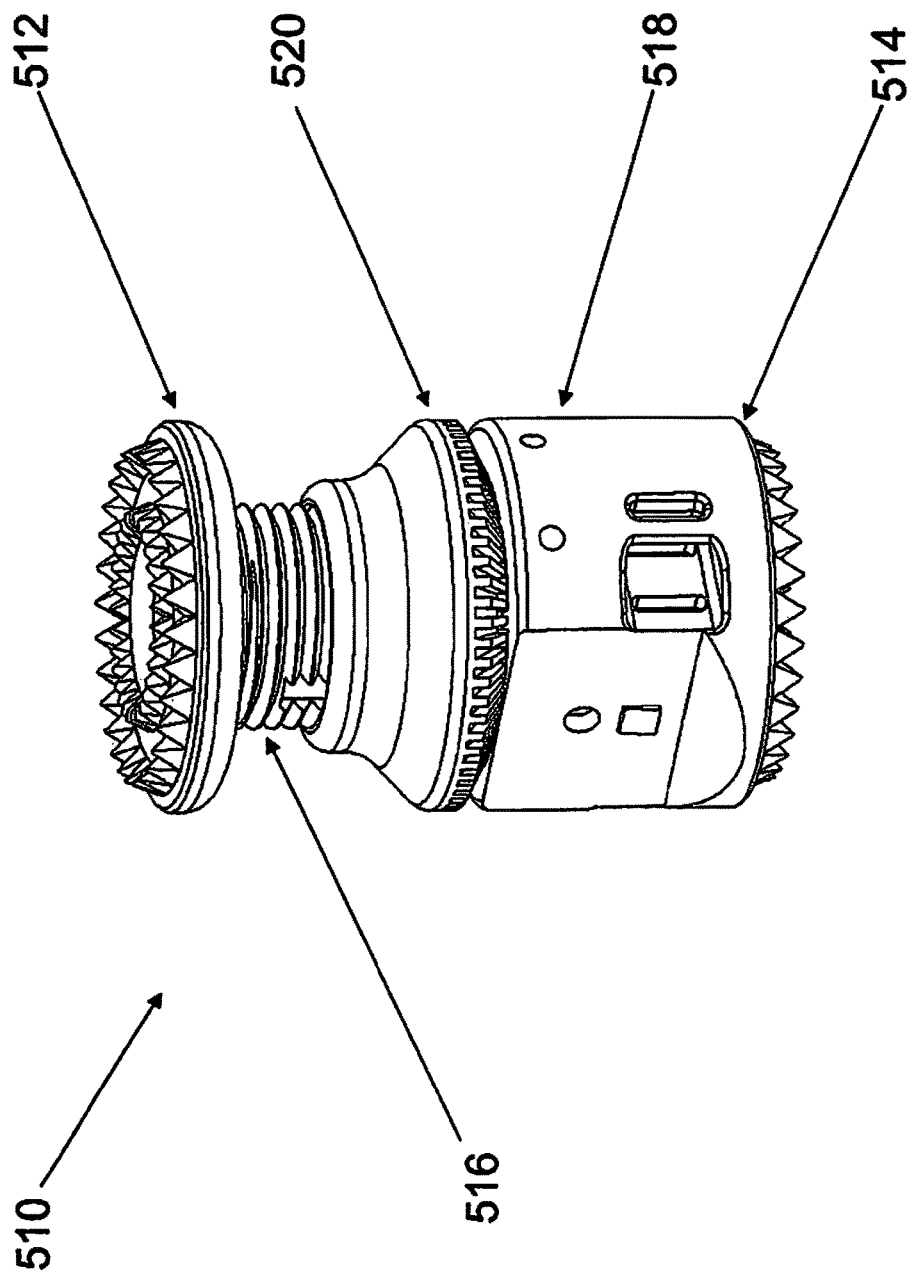
FIGS. 47-52 illustrate the locking assemblies according to the present invention.

FIGS. 47-52 show a self locking mechanism of the expandable prosthesis according to one embodiment of the present invention. FIG. 47 illustrates a prosthesis 510 having an upper and lower endplates 512, 514, wherein the upper endplate 512 is attached to an inner member 516 and the lower endplate 514 is attached to an outer member 518. The inner member 516 is threaded and translatable along the longitudinal axis. A gear member 520 is also illustrated having internal threads that are utilized to translate the inner member 516 along the longitudinal axis.

Figure 48:
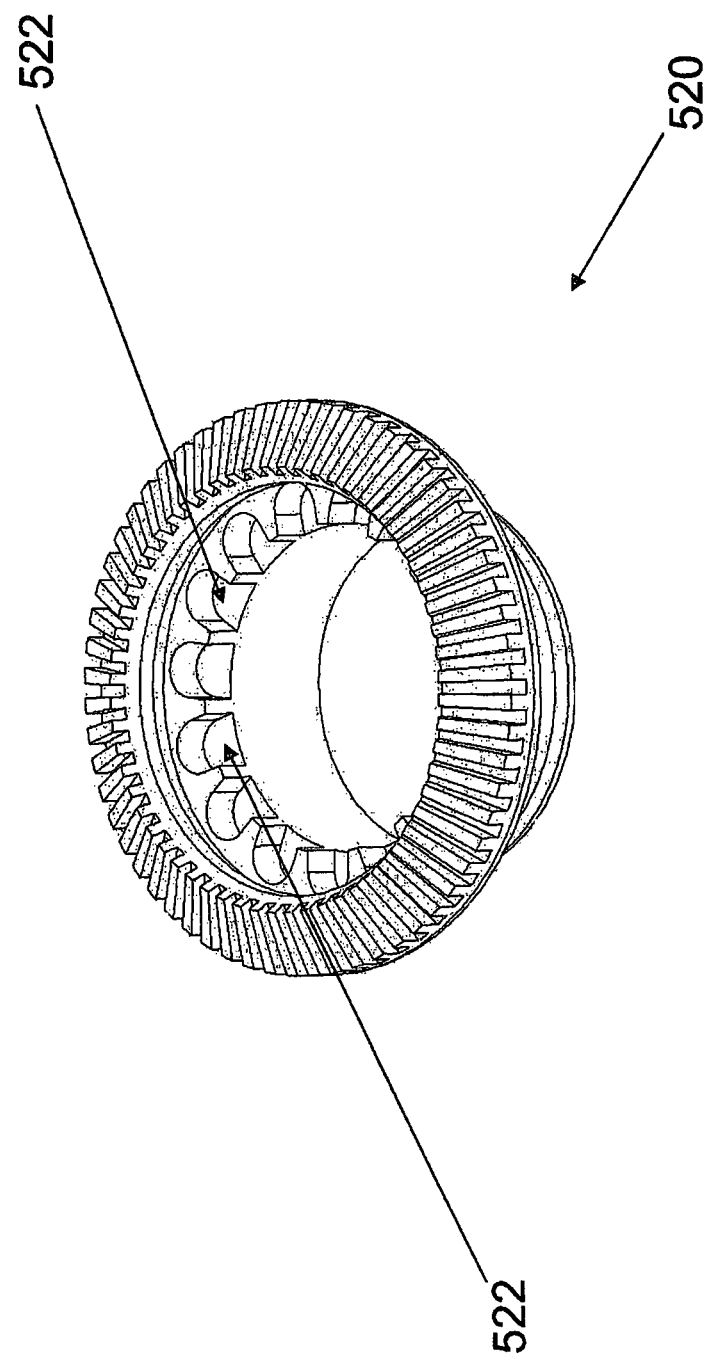

Now turning to FIG. 48, the gear member 520 is more clearly illustrated. The gear member 520 is provided with a plurality of gear teeth that is adapted to receive the first member of the prosthesis. On the inner portion of the gear member 520, there is provided a plurality of notches 522. The notches 522 are dimensioned and configured to receive a locking member. The locking mechanism of the present invention will be discussed in greater detail with reference to FIGS. 49-51.

Figure 49:
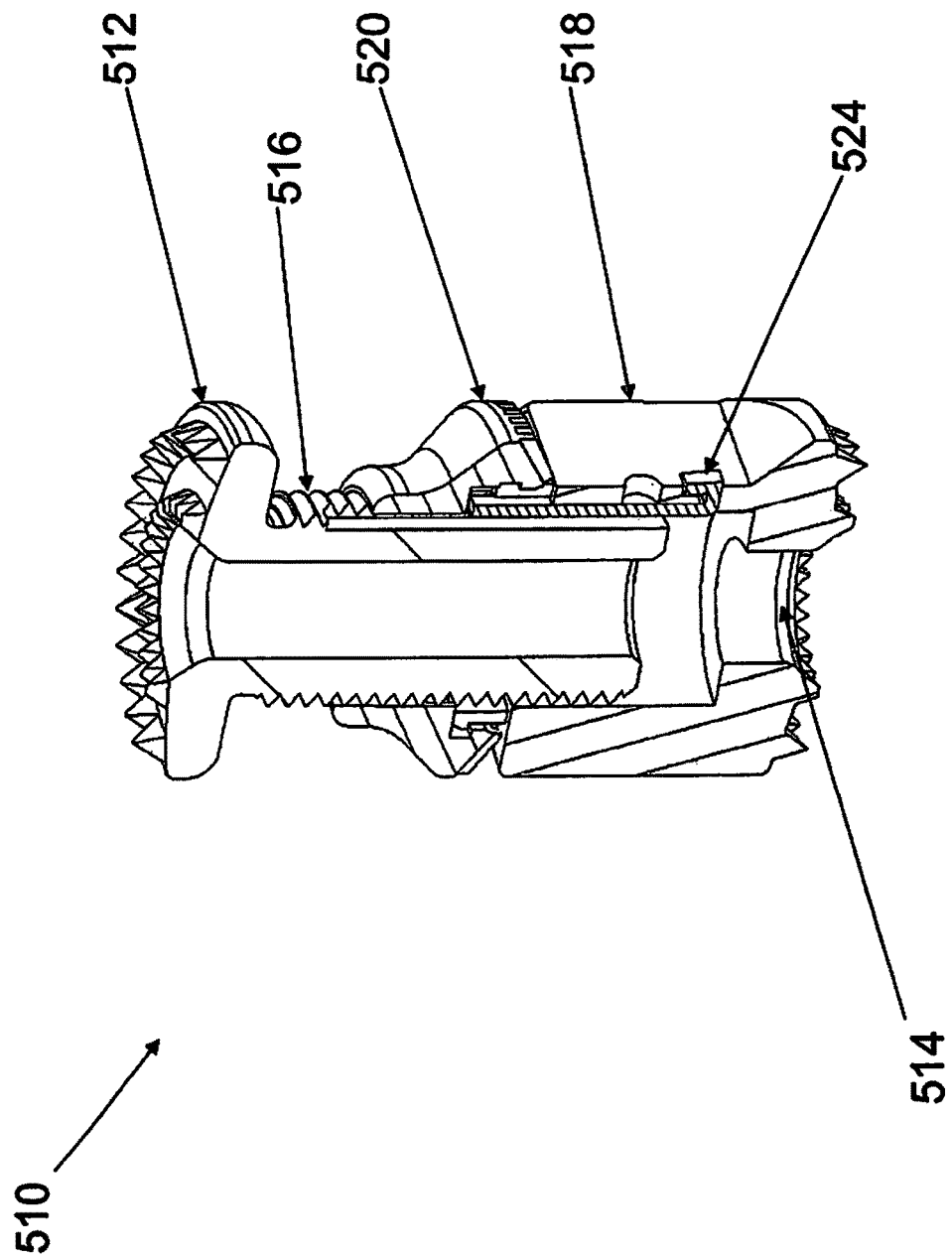
Figure 50:
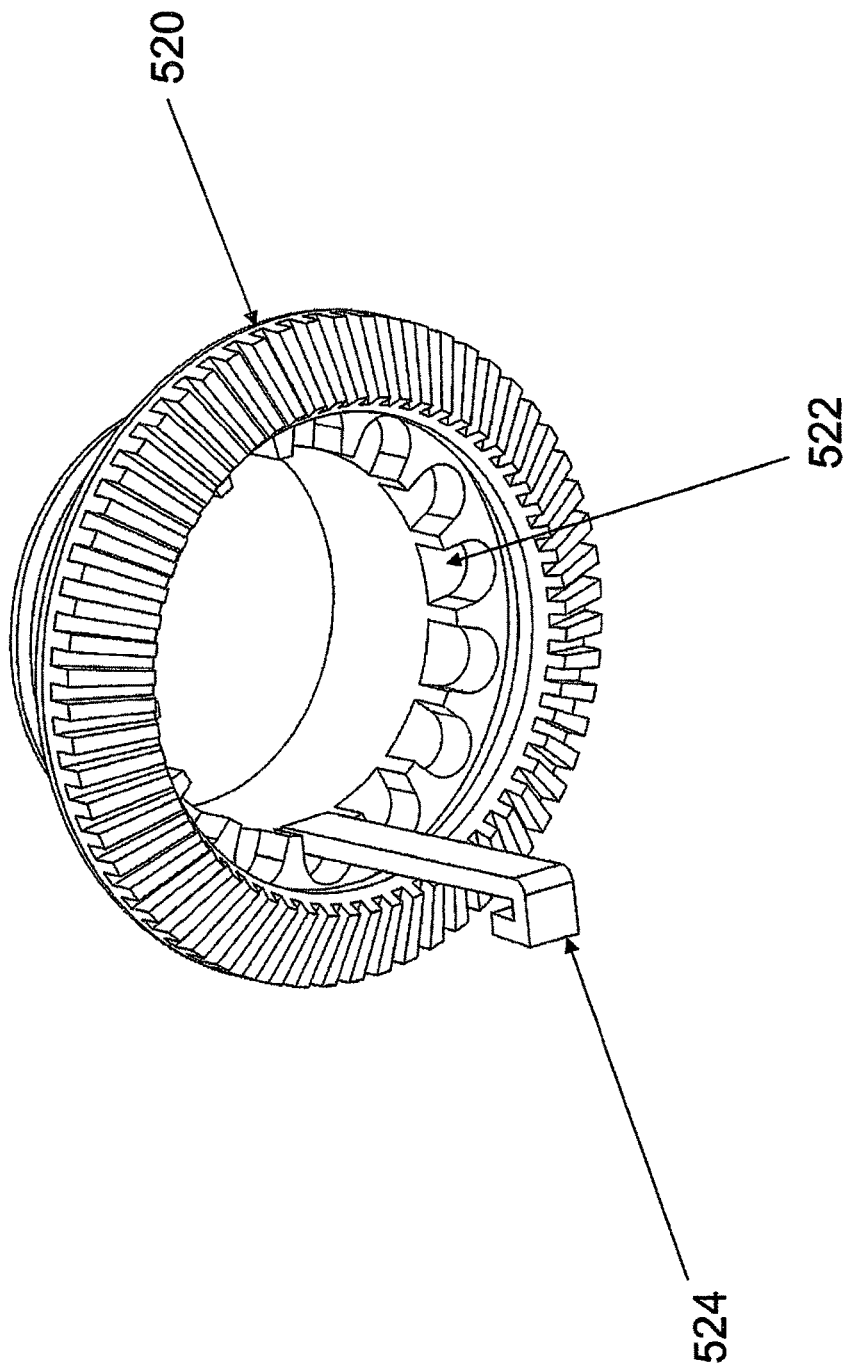
Figure 51:
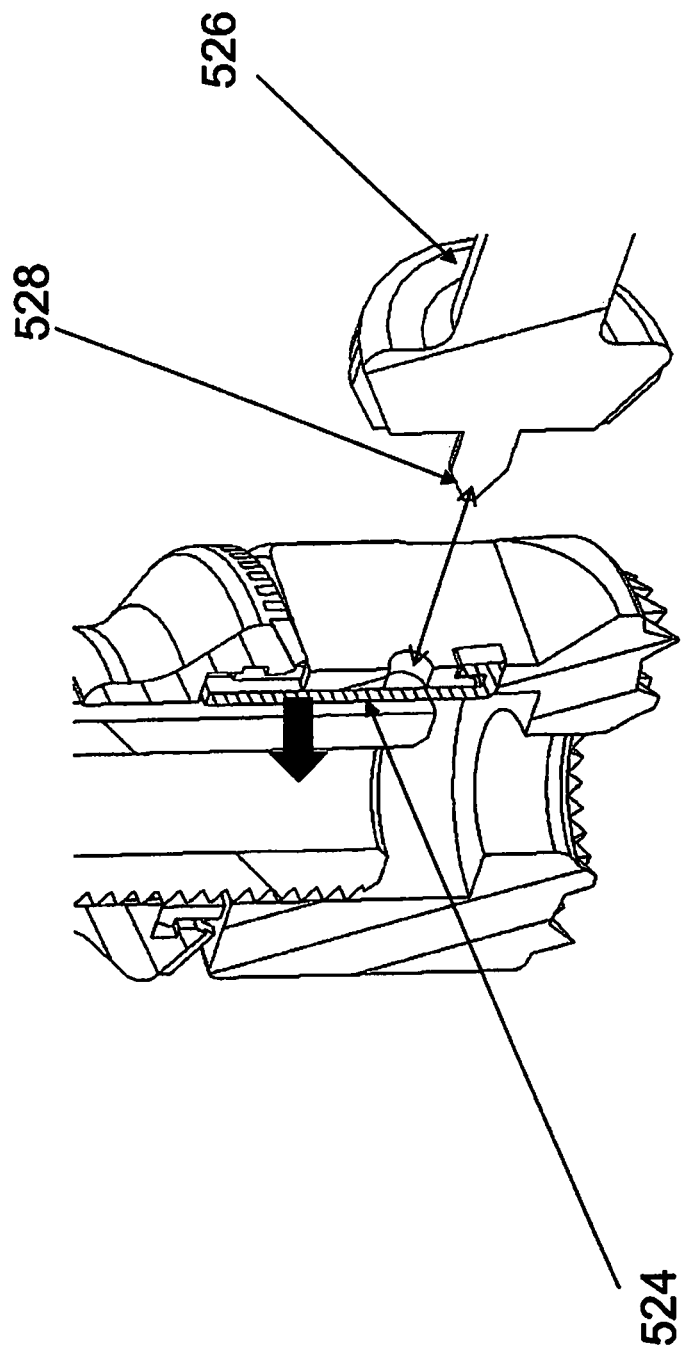

FIG. 49 illustrates a cross-section view of the prosthesis according to particular one embodiment of the present invention. More specifically, flexible member 524 is shown positioned between the outer member and the inner member of the prosthesis. The flexible member 524 is biased so that one end of the flexible member 524 is received within one of the plurality of notices of the gear member, as shown in FIG. 50. When the flexible member 524 is engaged with one of the notches 522 of the gear member, movement of the gear member 520 is blocked thereby blocking any relative movement between the inner member 516 and the outer member 518. When an inserter 526 with an insertion point 528 as shown in FIG. 51 is inserted into the outer member 518 of the implant, and the insertion point 528 applies pressure on the flexible member 524, and the flexible member 524 is moves radially so that the flexible member 524 disengages from the notch and allows the gear member 520 to be rotated. As a result, the gear member 520 allows relative movement between the inner member 516 and the outer member 518. When the insertion tool 526 is removed from implant, the flexible member 524 returns to its original position and engages with a notch within the gear member 520 and restricts the gear member 524 from rotating, thereby blocking relative movement between the inner member 516 and outer member 518.

Figure 52:
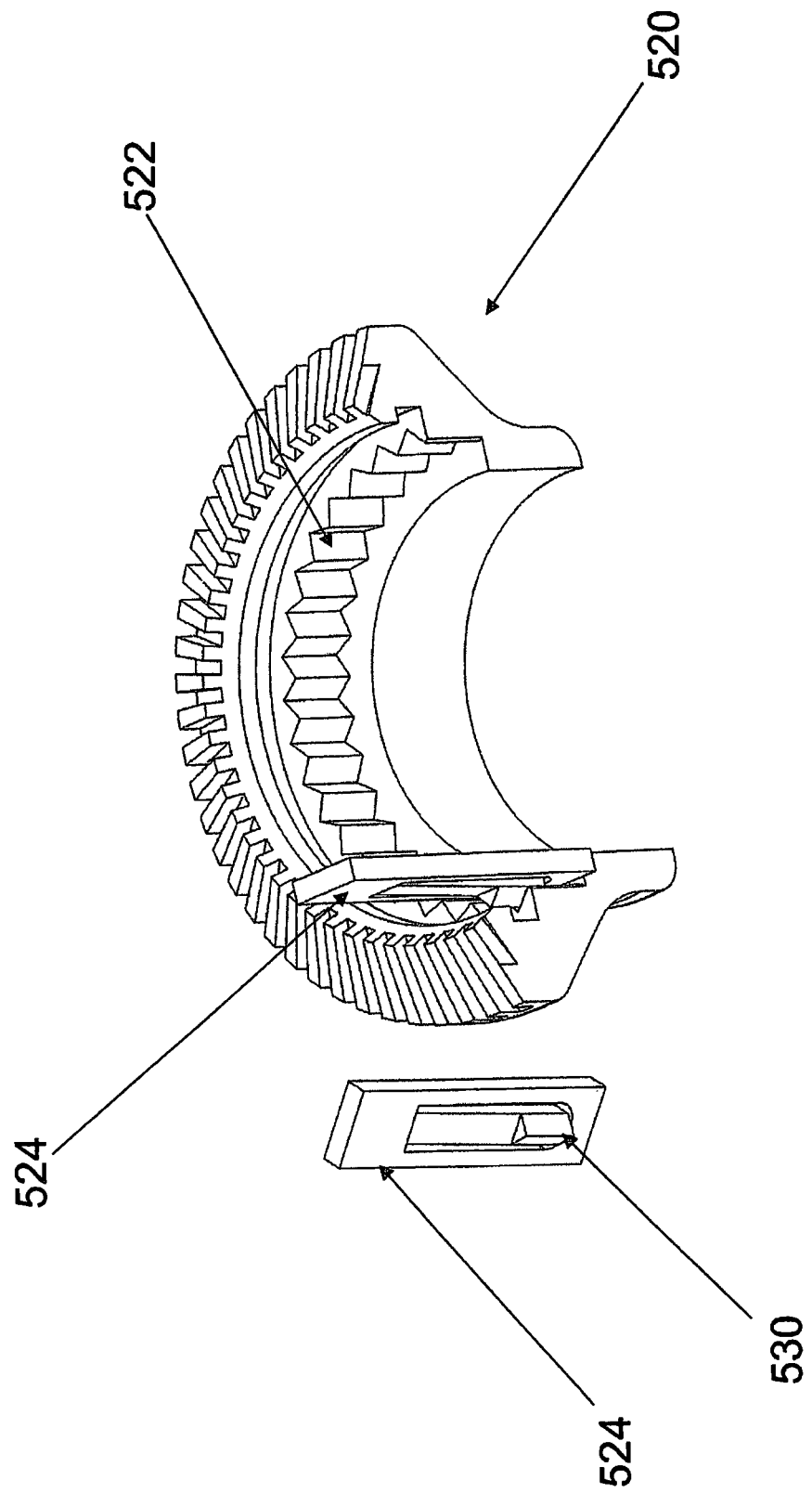

FIG. 52 illustrates another embodiment of the flexible member 524 according the present invention. In this embodiment, the member 524 is provided with a flexible portion 530 that couples with the angled notches 522 of the gear member 520. The member 524 may be used as a ratcheting device or in the alternative, any type of pressure applying device may be applied on the flexible portion 530 to disengage the member 524 from the angled notches 522.

It should be noted that any type of locking assembly that restricts the motion of the gear member after the implant is positioned is suitable in the present invention. For example, the locking assembly may utilize clips, springs, and/or any other type of biased members which can fit into the notches of the gear member to restrict motion may be used. It should also be noted that the notches may be of any general shape and size that couple with a portion of the flexible member.

While the invention herein disclosed has been described by means of specific embodiments and applications thereof, numerous modifications and variations can be made thereto by those skilled in the art without departing from the scope of the invention as set forth in the claims.

What is claimed is:

1. An expandable prosthetic implant system comprising:
a tool;
an outer member defining a hollow portion;
an inner member telescopically received within the hollow portion of the outer member such that the inner member and outer member are moveable relative to each other along a longitudinal axis, the inner member having a wall with an inner surface and an outer surface extending from a first end to a second end, the outer surface including external threads extending from the first end to the second end, and the inner member having a plurality of longitudinal slots extending radially through the wall from the inner surface to the outer surface; and
a gear member having a hollow body, the gear member having an inner wall and an outer wall, the inner wall having a helical thread along at least part of the inner wall, the outer wall having an array of gear teeth along a portion of the outer wall, the gear member positioned coaxial to the inner member and outer member such that the helical threads engage the external threads on the inner member and enable movement between the inner and outer members,
wherein lateral sides of the outer member are configured to engage opposing arms of the tool,
wherein the tool comprises a bevel gear for engaging the gear member, a central shaft positioned distally to the bevel gear, and a threaded distal tip portion extending distally from the central shaft, and wherein the tool is configured to expand and contract the expandable prosthetic implant by rotating the gear member while the opposing arms are engaged with the lateral sides of the outer member; and
wherein each opposing arm has a clamping portion and each clamping portion contains a plurality of teeth configured to facilitate a grip of the outer member, and
wherein the tool comprises one or more proximal ends configured to compress causing the opposing arms to actuate and receive the outer member.

2. The implant system of claim 1, wherein the outer member has a wall with an inner surface and an outer surface, and at least one pin protrudes radially inward from the inner surface of the outer member.

3. The implant system of claim 2, wherein the at least one pin engages with at least one of the plurality of longitudinal slots to prevent rotational movement of the inner member with respect to the outer member.

4. The implant system of claim 2, wherein the at least one pin extends into at least one of the plurality of longitudinal slots to ride within the longitudinal slot during expansion.

5. The implant system of claim 1, wherein the plurality of longitudinal slots are angularly spaced around the wall.

6. The implant system of claim 1, wherein the gear teeth are positioned at an angle with respect to a proximal end of the gear member.

7. The implant system of claim 6, wherein the gear teeth extend around the entire periphery of the gear member.

8. The implant system of claim 1, wherein the first end of the inner member includes a first end plate configured to engage a first vertebra.

9. The implant system of claim 8, wherein the first end plate has a generally elliptical shape when viewed perpendicular to the longitudinal axis.

10. The implant system of claim 8, wherein the first end plate is configured to rotate or pivot relative to the longitudinal axis.

11. The implant system of claim 1, wherein the outer member includes a second end plate configured to engage a second vertebra.

12. The implant system of claim 11, wherein the second end plate has a generally elliptical shape when viewed perpendicular to the longitudinal axis.

13. The implant system of claim 11, wherein the second end plate is configured to rotate or pivot relative to the longitudinal axis.

14. The implant system of claim 1, wherein the implant includes a locking member configured to restrict the gear member from rotating to block relative movement between the inner and outer members.

15. The implant system of claim 14, wherein the locking member protrudes radially inward from the outer member and is configured to engage the external threads of the inner member.

16. The implant system of claim 14, wherein the locking member is self-locking.

17. A system for an expandable prosthetic implant, the system comprising:
an expandable prosthetic implant comprising:
an outer member defining a hollow portion;
an inner member telescopingly received within the hollow portion of the outer member such that the inner member and outer member are moveable relative to each other along a longitudinal axis, the inner member having a wall with an inner surface and an outer surface extending from a first end to a second end, the outer surface including external threads extending from the first end to the second end, and the inner member having a plurality of longitudinal slots extending radially through the wall from the inner surface to the outer surface; and
a gear member having a hollow body, the gear member having an inner wall and an outer wall, the inner wall having a helical thread along at least part of the inner wall, the outer wall having an array of gear teeth along a portion of the outer wall, the gear member positioned coaxial to the inner member and outer member such that the helical threads engage the external threads on the inner member and enable movement between the inner and outer members; and
a tool configured to expand and contract the expandable prosthetic implant, the tool comprising:
a body extending along a tool axis, and in operation, the tool is configured to engage the expandable prosthetic implant such that the tool axis is generally perpendicular to the longitudinal axis;
a bevel gear having a plurality of teeth configured to engage the array of gear teeth on the gear member such that when the bevel gear is rotated, the gear member of the expandable prosthetic implant is rotated to expand or contract the expandable prosthetic implant;
a central shaft positioned distally to the bevel gear and having a threaded distal tip portion extending distally from the central shaft;
opposing arms, each arm having a clamping portion, configured to engage lateral sides of the expandable prosthetic implant to hold the expandable prosthetic implant between the clamping portions while allowing the bevel gear to rotate and expand the expandable prosthetic implant,
wherein each clamping portion has a plurality of teeth configured to facilitate a grip of the prosthetic implant, and
wherein the tool comprises one or more proximal ends configured to compress causing the opposing arms to actuate and receive the outer member.

18. The system of claim 17, wherein the threaded distal tip portion is configured to extend radially through a tool location hole in the outer member of the expandable prosthetic implant.

* * * * *